United States Patent [19]

Czajkowski et al.

[11] 4,003,735

[45] Jan. 18, 1977

[54] COMPOSITIONS AND METHODS FOR REDUCING HERBICIDAL INJURY

[75] Inventors: Albert J. Czajkowski, Maryland Heights; David E. Schafer, St. Louis, both of Mo.

[73] Assignee: Monsanto Company, St. Louis, Mo.

[22] Filed: Nov. 4, 1974

[21] Appl. No.: 520,521

[52] U.S. Cl. .................................. 71/101; 71/88; 71/94; 71/95; 71/98; 71/100; 71/106; 71/111; 71/118

[51] Int. Cl.² ......................................... A01N 9/12

[58] Field of Search ........................... 71/101, 118

[56] References Cited

UNITED STATES PATENTS

| 2,863,752 | 12/1958 | Hamm et al. | 71/118 |
|---|---|---|---|
| 3,131,509 | 5/1964 | Hoffman | 71/79 |
| 3,133,810 | 5/1964 | Hamm | 71/118 |
| 3,161,496 | 12/1964 | D'Amico | 71/101 |
| 3,663,200 | 5/1972 | Olin | 71/118 |
| 3,719,466 | 3/1973 | Ahle | 71/118 |
| 3,832,383 | 8/1974 | Olin | 71/111 |
| 3,867,444 | 2/1975 | Baker | 71/118 |

FOREIGN PATENTS OR APPLICATIONS 1,180,472   4/1970   United Kingdom ............... 71/111

*Primary Examiner*—Glennon H. Hollrah
*Attorney, Agent, or Firm*—William I. Andress; Donald W. Peterson

[57] ABSTRACT

A method and compositions for reducing injury to crops, especially wheat and sorghum, by acetanilide selective herbicides employing compounds having in common the base structure

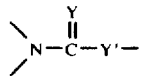

wherein Y and Y' are oxygen or sulfur.

30 Claims, No Drawings

COMPOSITIONS AND METHODS FOR REDUCING HERBICIDAL INJURY

This invention relates to novel compositions and methods for reducing or nullifying injury to young crop plants by selective herbicides. More specifically, this invention relates to novel compositions and methods for reducing injury to young crop plants by selective herbicides, such as acetanilide herbicides, which comprises treating the habitat of the crop plant or the seed of the crop plant prior to planting, with an antagonistic agent for the selective herbicide.

The acetanilide herbicides such as alachlor, propachlor, butachlor and the like are very useful for controlling certain weeds in the presence of other growing plants. However, many of these herbicides injure certain crop plants, slowing growth and development at application rates necessary to stunt or kill the weeds. As a consequence, certain of these herbicides can not be employed for controlling weeds in the presence of certain crops, some of which crops are important commodities in the world food supply. Obviously, there is a need for a method of reducing or nullifying the injury of the crop plant by the selective acetanilide herbicide while not affecting the herbicidal action on the weed to be controlled.

There is provided by this invention a novel method of reducing or nullifying injury to the desired crop plant by selective acetanilide herbicides which does not interfere with the herbicidal action on the weed to be controlled. There are also provided novel compositions for treating the soil or the crop seed to reduce or nullify injury to the crop by selective acetanilide herbicides.

The compounds which are useful in reducing or eliminating crop injury are sometimes referred to as antagonistic agents, antidote compounds, or safening agents. Antagonistic agents for the purpose of this invention are defined as compounds which counteract the herbicidal action of selective acetanilide herbicides, thereby reducing or nullifying injury to the plant, yet, which exhibit little or no toxicity to the crop or crop seed at effective rates of application. Although the mechanism by which these compounds reduce the herbicidal activity of the acetanilide herbicide on crop plants without reducing the effective control of undesired plants or weeds, is not fully understood, the herbicide test program has confirmed the phenomenon for a wide variety of compounds having in common the base structure

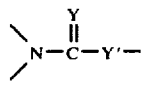

wherein Y and Y' are oxygen or sulfur. These compounds when employed with an acetanilide herbicide reduced the injury to crop plants by the acetanilide herbicide, particularly the injury to wheat and sorghum. The compounds which are preferred antagonistic agents with acetanilide hericides for the selective control of undesired plants in the presence of wheat and sorghum are described by the formula

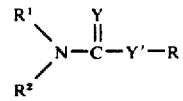

wherein Y and Y' are each independently oxygen or sulfur and, when Y and Y' are both oxygen, R is alkyl, alkenyl, haloalkenyl or haloalkynyl. $R^1$ is hydrogen, alkyl or alkenyl and $R^2$ is alkyl, phenyl or substituted phenyl, or $R^1$ and $R^2$ when taken together are alkylene of the emperical formula —$C_nH_{2n}$— wherein $n$ is an integer of from 4 through 8, inclusive, having from 4 through 8 carbons in a continuous chain between the nitrogen terminal bonds or a group of the formula —$C_2H_4OC_2H_4$—; when one of Y and Y' is oxygen, R is alkyl, alkenyl or haloalkenyl, $R^1$ is hydrogen, alkyl or

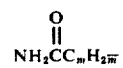

wherein $m$ is an integer of from 1 to 4 and $R^2$ is hydrogen, alkyl, phenyl or substituted phenyl or $R^1$ and $R^2$ when taken together are a group of the formula —$C_2H_4OC_2H_4$—or $R^1$ and $R^2$ when taken together, provided that Y is oxygen, are alkylene of the empirical formula —$C_nH_{2n}$— wherein $n$ is an integer of from 4 through 8, inclusive, having from 4 through 8 carbons in a continuous chain between the nitrogen terminal bonds, or $R^1$ and $R^2$ when taken together, provided that Y' is oxygen, are an unsaturated hydrocarbon of the empirical formula —$C_nH_{2n-2}$ wherein n is an integer of from 4 through 8, inclusive, having from 4 through 8 carbons in a continuous chain between the nitrogen terminal bonds; and when both Y an Y' are sulfur, R is alkyl, substituted alkyl, alkenyl, haloalkenyl, phenyl or substituted phenyl, $R^1$ is alkyl, phenyl or substituted phenyl and $R^2$ is hydrogen, alkyl, alkenyl or haloalkenyl or R and $R^1$ when taken together are alkylene of the empirical formula —$C_nH_{2n}$— wherein n is an integer of from 4 through 8, inclusive, having from 4 through 8 carbons in a continuous chain between the nitrogen terminal bonds, an unsaturated hydrocarbon of the empirical formula —$C_nH_{2n-2}$ wherein $n$ is an integer of from 4 through 8, inclusive, having from 4 through 8 carbons in a continuous chain between the nitrogen terminal bonds or a group of the formula

wherein each $R^3$ is independently hydrogen, halo or lower alkyl.

The amount of such antagonistic agents employed in methods and compositions of this invention will vary according to the particular acetanilide herbicide with which the agent is employed and the rate of application of the herbicide. In each instance the amount of antagonistic agent employed is a safening effective amount. By a safening effective amount is meant an amount which reduces crop injury by the acetanilide herbicide. In the tests employed in illustrating this invention, the amount of crop injury was reduced by at least 15 percent. In certain instances, a significant level of reduction of crop injury may be as low as about 10 percent and in other instances no lower than 20 percent. The reduction in level of crop injury is defined as the difference between the observed percentage of crop injury by the acetanilide herbicide without the safening agent and the observed percentage of crop injury by the acetanilide herbicide employed in conjunction with a safening effective amount of an antagonistic agent as defined herein.

Preferred alkyl are aliphatic hydrocarbons having from 1 through 18, inclusive, carbons. The configuration of the structure can be straight-chain, branched-chain, cyclic or a mixed configuration having both branched and cyclic moieties. More preferred alkyl have from 1 through 6, inclusive, carbons.

As employed herein, the terms "lower alkyl" and "lower alkoxy" designate those groups wherein the aliphatic chain is straight or branched and has from 1 through 4 carbons, inclusive.

As employed herein, the term "substituted phenyl" designates phenyl groups of the formula

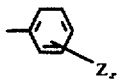

wherein each Z is independently halo, trihalomethyl, hydroxyl, nitro, lower alkyl or lower alkoxy, and $x$ is an integer from 1 through 3, inclusive, provided that no more than two Z's are nitro and that no more than one Z is hydroxyl. The term "halo" designates a halogen atom selected from fluorine, chlorine, bromine and iodine. Preferred halo are chloro and bromo. Preferred trihalomethyl is trifluoromethyl.

Preferred alkenyl have from 2 through 8, inclusive, carbons. More preferred alkenyl have from 3 through 6, inclusive, carbons. Still more preferred alkenyl have 3 carbons and have the unsaturated bond in the 2-position.

Preferred haloalkenyl have from 2 through 8, inclusive, carbons and 1 through 3, inclusive, halogens. More preferred haloalkenyl have from 3 through 6, inclusive, carbons and 1 through 3, inclusive, halogens. Still more preferred haloalkenyl have from 3 through 6, inclusive, carbons and 1 through 3, inclusive, chlorines.

Preferred haloalkynyl have from 2 through 8, inclusive, carbons and 1 through 3, inclusive, halogens. More preferred haloalkynyl have from 3 through 6, inclusive, carbons and 1 through 3, inclusive, halogens. Still more preferred haloalkynyl have from 3 through 6, inclusive, carbons and 1 through 3, inclusive, chlorines.

Preferred substituted alkyl have from 1 through 3, inclusive, substituents selected from the group consisting of cyano; hydroxyl, phenyl, substituted phenyl, phenoxyl and substituted phenoxyl. More preferred substituted alkyl have, in the aliphatic portion of the group, from 1 through 6, inclusive, carbons. Still more preferred substituted alkyl have one substituent selected from the aforementioned group.

The compounds employed herein as antagonistic agents are either known compounds or are readily prepared from known compounds by old methods known to the skilled chemist.

Acetanilide herbicides are widely known in the art. U.S. Pat. No. 2,863,752, 3,442,945, 3,547,620, 3,630,716, and 3,637,847 are but a few of the many patents disclosing acetanilide herbicides which have published in the United States and other countries.

Although it has been taught that a wide variety of acetanilides are useful as selective herbicides, it is evident from the prior art that alpha-haloacetanilides are most commercially significant herbicidal acetanilides. Because of the wide usage of alpha-haloacetanilides, these herbicides are the preferred herbicides for safening by the methods and compositions of the present invention. Nevertheless, the present safening methods and compositions are useful for safening the herbicidal acetanilide family of compounds and the instant invention is not limited to only alpha-haloacetanilide herbicides.

Particularly effective safening properties are obtained with selective alpha-haloacetanilides of the formula

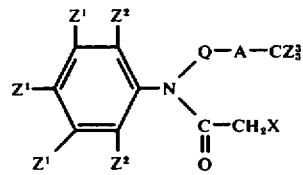

wherein X is halo, Q is alkylene of the empirical formula $-C_yH_{2y}$ wherein $y$ is an integer of from 1 through 8, inclusive, A is oxygen or sulfur, each $Z^3$ independently is hydrogen, alkyl, alkenyl, alkynyl, alkoxy, polyalkoxy, alkoxyalkyl, polyalkoxyalkyl, haloalkyl, hydroxyalkyl, haloalkenyl, oxoalkyl, alkenyloxy and alkyl each of a maximum of 18 carbon atoms; aryl, aryloxyalkyl, haloaryl, haloaryloxyalkyl and arylalkyl of from 6 to 24 carbon atoms; furfuryl; and tetrahydrofurfuryl; or two groups are combined to form a cyclic group of from 2 to 6 carbon atoms selected from the group consisting of

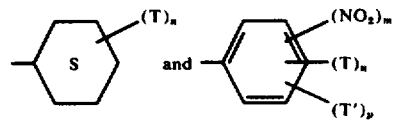

wherein T is chlorine, bromine or fluorine, T' is alkyl of a maximum of 6 carbon atoms or acyl of a maximum of 4 carbon atoms, $m$ is an integer of from 0 to 3, inclusive, $n$ is an integer of from 0 to 5, inclusive, and $p$ is an integer of 0 or 1 and each $Z^1$ independently is hydrogen, halogen, or alkyl each of a maximum of 10 carbon atoms, and each $Z^2$ independently is hydrogen, alkyl or alkoxy each of a maximum of 10 carbon atoms.

Particularly good safening of alachlor, propachlor and butachlor herbicides with regard to wheat and sorghum has been found employing the safening methods and compositions of the present invention. These particularly good results with regard to wheat and sorghum are likewise obtained with herbicides of the formula

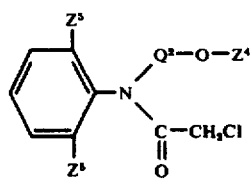

wherein each $Z^5$ is independently lower alkyl or hydrogen, $Z^4$ is lower alkyl and $Q^2$ is alkylene of the empirical formula $-C_zH_{2z}-$ wherein z is an integer of from 1 through 4, inclusive, preferably from 1 through 4, inclusive.

The method and compositions of this invention are illustrated by the following examples.

EXAMPLES 1 THROUGH 180

The safening effectiveness of representative antagonistic agents on representative acetanilide herbicides with respect to wheat and sorghum is shown by the test results presented in Table I. For each antagonistic agent, there is shown the percent inhibition of the plants by the acetanilide herbicide and the antagonistic agent and the safening effect of the antagonistic agent in terms of reduction in percent control which is determined by subtracting the percent control of the acetanilide herbicide in a specified amount and the antagonistic agent in a specified amount from the percent control of the acetanilide herbicide in the same specified amount but with no antagonistic agent. These results are obtained by the following procedure:

A good grade of top soil is placed in an aluminum pan and compacted to a depth of ⅜ to ½ inch from the top of the pan. A predetermined number of seeds of each of the plant species to be tested are placed on top of the soil in the pans. A quantity of soil sufficient to substantially fill the pan is measured and placed in suitable container. A measured quantity of the antagonistic agent dispersed or dissolved in a suitable carrier is sprayed on the soil in the container. A measured quantity of the acetanilide herbicide dispersed or dissolved in a suitable carrier is then sprayed on the soil in the container already treated with the safening agent.

The quantity of acetanilide herbicide and antagonistic agent is expressed in terms of kilograms per hectare for ease of comparing the greenhouse test results with field results. The soil containing the antagnostic agent and acetanilide herbicide is thoroughly mixed. This mixing is sometimes referred to as incorporation of the herbicide and antagonistic agent into the soil. The mixing or incorporation provides a substantially uniform distribution of the antagonistic agent and herbicide throughout the soil. The seeds are covered with the soil containing the antagonistic agent and acetanilide herbicide and the pans are leveled. The pans are then placed on a sand bench in the greenhouse and watered from below as needed. The plants are observed at the end of approximately 21 days and the results in terms of percent inhibition of each seed lot are recorded. For each test series a pan of plants is also prepared containing no acetanilide herbicide and no antagonistic agent as a control. Additionally, for each test, a pan of plants is prepared with soil covering the seed containing no acetanilide herbicide and only the measured amount of antagonistic agent being incorporated into the soil covering the seeds to ascertain any herbicidal effect of the antagonistic agent alone. For each series of tests the herbicidal effect of the acetanilide herbicide is observed from pans of plants treated with the same quantity of herbicide alone.

TABLE I (A)

| Example No. | Amount of alachlor Herbicide (kg./ha.) | Antagonistic Agent | Amount (kg./ha.) | Crop | Percent Inhibition | Safening Effect (%) |
| --- | --- | --- | --- | --- | --- | --- |
| 1 | 0.14 | Ethyl-N-isopropyl-carbamate | 4.48 | Wheat | 10 | 13 |
|   | 0.14 | Ethyl-N-isopropyl-carbamate | 4.48 | Sorghum | 0 | 35 |
| 2 | 0.14 | Ethylisobutyl-carbamate | 4.48 | Wheat | 10 | 13 |
|   | 0.14 | Ethylisobutyl-carbamate | 4.48 | Sorghum | 15 | 20 |
| 3 | 0.14 | Ethyl-1,2-dimethyl-butylcarbamate | 4.48 | Wheat | 0 | 23 |
|   | 0.14 | Ethyl-1,2-dimethyl-butylcarbamate | 4.48 | Sorghum | 15 | 20 |
| 4 | 0.14 | Ethyl-N-ethyl,N-t-butyl-thiolcarbamate | 4.48 | Wheat | 0 | 23 |
|   | 1.12 | Ethyl-N-ethyl,N-t-butyl-thiolcarbamate | 4.48 | Wheat | 10 | 25 |
| 5 | 0.14 | Ethyldimethyl-thionocarbamate | 4.48 | Wheat | 0 | 23 |
|   | 0.14 | Ethyldimethyl-thionocarbamate | 4.48 | Sorghum | 15 | 20 |
| 6 | 0.14 | Butylcarbanilate | 4.48 | Wheat | 0 | 5 |
|   | 0.14 | Butylcarbanilate | 4.48 | Sorghum | 30 | 35 |
| 7 | 0.14 | Methylcarbanilate | 4.48 | Sorghum | 40 | 25 |

TABLE I (A)-continued

| Example No. | Amount of alachlor Herbicide (kg./ha.) | Antagonistic Agent | Amount (kg./ha.) | Crop | Percent Inhibition | Safening Effect (%) |
|---|---|---|---|---|---|---|
| 8 | 0.14 | Isopropyl-N-butyl-carbanilate | 4.48 | Sorghum | 10 | 55 |
|  | 1.12 | Isopropyl-N-butyl-carbanilate | 4.48 | Sorghum | 40 | 60 |
| 9 | 0.14 | Butylthiol-carbanilate | 2.24 | Sorghum | 10 | 55 |
| 10 | 0.14 | Methyl-N-methylthiol-carbanilate | 4.48 | Sorghum | 35 | 30 |
|  | 1.12 | Methyl-N-methylthiol-carbanilate | 4.48 | Sorghum | 80 | 20 |
| 11 | 1.12 | Methyl-thiono-carbanilate | 4.48 | Sorghum | 75 | 25 |
| 12 | 1.12 | Methyl-2,6-diethyl-thionocarbanilate | 4.48 | Sorghum | 80 | 20 |
| 13 | 1.12 | Allyl-N-ethyldithio-carbanilate | 4.48 | Sorghum | 70 | 30 |
| 14 | 0.14 | Butyl-N-ethyldithio-carbanilate | 4.48 | Sorghum | 35 | 30 |
|  | 1.12 | Butyl-N-ethyldithio-carbanilate | 4.48 | Sorghum | 80 | 20 |
| 15 | 0.14 | Methyl-N-ethyldithio-carbanilate | 4.48 | Sorghum | 5 | 60 |
|  | 1.12 | Methyl-N-ethyldithio-carbanilate | 4.48 | Sorghum | 35 | 65 |
| 16 | 0.14 | Hexyl-N-ethyldithio-carbanilate | 4.48 | Wheat | 0 | 5 |
|  | 1.12 | Hexyl-N-ethyldithio-carbanilate | 4.48 | Wheat | 0 | 20 |
|  | 0.14 | Hexyl-N-ethyldithio-carbanilate | 4.48 | Sorghum | 25 | 40 |
| 17 | 0.14 | Methyldithiocarbanilate | 4.48 | Sorghum | 35 | 30 |
| 18 | 0.14 | 2-chloro-allyl-N-methyldithiocarbanilate | 4.48 | Sorghum | 35 | 30 |
|  | 1.12 | 2-chloro-allyl-N-methyldithiocarbanilate | 4.48 | Sorghum | 75 | 25 |
| 19 | 1.12 | 2-chloro-ethyl-N-ethylthionocarbanilate | 4.48 | Sorghum | 65 | 35 |
| 20 | 0.28 | Ethyl-N-isopropyl-carbamate | 4.48 | Wheat | 0 | 30 |
|  | 0.56 | Ethyl-N-isopropyl-carbamate | 4.48 | Wheat | 10 | 30 |
| 21 | 0.28 | Ethyldimethylthionocarbamate | 4.48 | Wheat | 0 | 30 |
|  | 0.56 | Ethyldimethylthionocarbamate | 4.48 | Wheat | 10 | 30 |
|  | 1.12 | Ethyldimethylthionocarbamate | 4.48 | Wheat | 10 | 15 |
|  | 2.24 | Ethyldimethylthionocarbamate | 4.48 | Wheat | 20 | 10 |
|  | 0.28 | Ethyldimethylthionocarbamate | 4.48 | Sorghum | 45 | 28 |
| 22 | 0.28 | Ethylisobutylcarbamate | 4.48 | Wheat | 0 | 30 |
|  | 0.56 | Ethylisobutylcar- | 4.48 | Wheat | 20 | 20 |

TABLE I (A)-continued

| Example No. | Amount of alachlor Herbicide (kg./ha.) | Antagonistic Agent | Amount (kg./ha.) | Crop | Percent Inhibition | Safening Effect (%) |
|---|---|---|---|---|---|---|
| | 1.12 | Ethylisobutylcarbamate | 4.48 | Wheat | 10 | 15 |
| | 2.24 | Ethylisobutylcarbamate | 4.48 | Wheat | 20 | 10 |
| | 0.28 | Ethylisobutylcarbamate | 4.48 | Sorghum | 55 | 18 |
| 23 | 0.28 | Isopropyl-N-butylcarbanilate | 4.48 | Sorghum | 25 | 48 |
| | 0.56 | Isopropyl-N-butylcarbanilate | 4.48 | Sorghum | 75 | 20 |
| | 1.12 | Isopropyl-N-butylcarbanilate | 4.48 | Sorghum | 60 | 38 |
| | 2.24 | Isopropyl-N-butylcarbanilate | 4.48 | Sorghum | 60 | 35 |
| 24 | 0.28 | 2-chloroallyl-p-methylthiolcarbanilate | 4.48 | Sorghum | 50 | 23 |
| | 0.56 | 2-chloroallyl-p-methylthiolcarbanilate | 4.48 | Sorghum | 65 | 30 |
| 25 | 0.28 | Methyl-N-ethyldithiocarbanilate | 4.48 | Sorghum | 15 | 58 |
| | 0.56 | Methyl-N-ethyldithiocarbanilate | 4.48 | Sorghum | 35 | 60 |
| | 1.12 | Methyl-N-ethyldithiocarbanilate | 4.48 | Sorghum | 35 | 63 |
| | 2.24 | Methyl-N-ethyldithiocarbanilate | 4.48 | Sorghum | 70 | 25 |
| 26 | 0.28 | Hexyl-N-ethyldithiocarbanilate | 4.48 | Wheat | 10 | 20 |
| | 0.56 | Hexyl-N-ethyldithiocarbanilate | 4.48 | Wheat | 20 | 20 |
| 27 | 0.28 | Methyl-N-ethyldithiocarbanilate | 0.28 | Sorghum | 65 | 20 |
| | 0.28 | Methyl-N-ethyldithiocarbanilate | 1.12 | Sorghum | 45 | 40 |
| | 0.28 | Methyl-N-ethyldithiocarbanilate | 4.48 | Sorghum | 10 | 75 |
| | 0.56 | Methyl-N-ethyldithiocarbanilate | 1.12 | Sorghum | 35 | 53 |
| | 0.56 | Methyl-N-ethyldithiocarbanilate | 4.48 | Sorghum | 25 | 63 |
| | 1.12 | Methyl-N-ethyldithiocarbanilate | 4.48 | Sorghum | 35 | 60 |
| | 2.24 | Methyl-N-ethyldithiocarbanilate | 4.48 | Sorghum | 50 | 45 |
| 28 | 0.28 | Isobutyl-N-butylcarbanilate | 4.48 | Sorghum | 20 | 65 |
| | 0.56 | Isobutyl-N-butylcarbanilate | 4.48 | Sorghum | 30 | 58 |
| | 1.12 | Isobutyl-N-butylcarbanilate | 4.48 | Sorghum | 20 | 75 |
| | 2.56 | Isobutyl-N-butylcarbanilate | 4.48 | Sorghum | 65 | 30 |
| 29 | 0.28 | Isobutylcarbanilate | 4.48 | Sorghum | 15 | 60 |
| | 0.84 | Isobutylcarbanilate | 4.48 | Sorghum | 60 | 30 |
| | 1.12 | Isobutylcarbanilate | 4.48 | Sorghum | 65 | 25 |
| 30 | 0.28 | t-butyl- | 4.48 | Sorghum | 40 | 35 |

TABLE I (A)-continued

| Example No. | Amount of alachlor Herbicide (kg./ha.) | Antagonistic Agent | Amount (kg./ha.) | Crop | Percent Inhibition | Safening Effect (%) |
|---|---|---|---|---|---|---|
| | 0.84 | carbanilate t-butyl-carbanilate | 4.48 | Sorghum | 70 | 20 |
| 31 | 0.28 | t-butyl-thiolcarbanilate | 4.48 | Sorghum | 60 | 15 |
| | 0.84 | t-butyl-thiolcarbanilate | 4.48 | Sorghum | 75 | 15 |
| 32 | 0.28 | Sec-butyl-N-ethyldithiocarbanilate | 4.48 | Sorghum | 55 | 20 |
| 33 | 2.24 | Ethyl-N-ethyldithiocarbanilate | 4.48 | Wheat | 30 | 45 |
| | 0.28 | Ethyl-N-ethyldithiocarbanilate | 4.48 | Sorghum | 35 | 53 |
| | 0.84 | Ethyl-N-ethyldithiocarbanilate | 4.48 | Sorghum | 40 | 53 |
| | 2.24 | Ethyl-N-ethyldithiocarbanilate | 4.48 | Sorghum | 75 | 23 |
| 34 | 2.24 | Propyl-N-ethyldithiocarbanilate | 4.48 | Wheat | 15 | 60 |
| | 0.28 | Propyl-N-ethyldithiocarbanilate | 4.48 | Sorghum | 45 | 43 |
| 35 | 2.24 | Butyldithiocarbanilate | 2.24 | Wheat | 35 | 40 |
| | 0.28 | Butyldithiocarbanilate | 2.24 | Sorghum | 60 | 28 |
| 36 | 0.28 | Methyl-N-isopropyl-thiolcarbanilate | 2.24 | Sorghum | 50 | 38 |
| | 0.84 | Methyl-N-isopropyl-thiolcarbanilate | 2.24 | Sorghum | 70 | 23 |
| 37 | 0.28 | Isopropyl-N-propyl-thiolcarbanilate | 0.56 | Sorghum | 75 | 13 |
| | 0.84 | Isopropyl-N-propyl-thiolcarbanilate | 0.56 | Sorghum | 75 | 18 |
| 38 | 0.28 | t-butyl-N-isopropyl-thiolcarbanilate | 4.48 | Sorghum | 40 | 48 |
| | 0.84 | t-butyl-N-isopropyl-thiolcarbanilate | 4.48 | Sorghum | 60 | 33 |
| | 2.24 | t-butyl-N-isopropyl-thiolcarbanilate | 4.48 | Sorghum | 70 | 28 |
| 39 | 0.28 | Ethyl-N-t-butylcarbanilate | 4.48 | Sorghum | 45 | 43 |
| | 0.84 | Ethyl-N-t-butylcarbanilate | 4.48 | Sorghum | 75 | 18 |
| 40 | 2.24 | Propyl-N-isopropyl-dithiocarbanilate | 4.48 | Sorghum | 50 | 25 |
| 41 | 0.28 | Allylthionocarbanilate | 4.48 | Wheat | 0 | 20 |
| | 0.84 | Allylthionocarbanilate | 4.48 | Wheat | 0 | 65 |
| | 2.24 | Allylthionocarbanilate | 4.48 | Wheat | 0 | 70 |
| | 0.28 | Allylthionocarbanilate | 4.48 | Sorghum | 20 | 30 |
| | 0.84 | Allylthionocarbanilate | 4.48 | Sorghum | 40 | 55 |
| | 2.24 | Allylthionocarbanilate | 4.48 | Sorghum | 75 | 19 |
| 42 | 0.28 | 2-methylallylcarbanilate | 4.48 | Wheat | 0 | 20 |

TABLE I (A)-continued

| Example No. | Amount of alachlor Herbicide (kg./ha.) | Antagonistic Agent | Amount (kg./ha.) | Crop | Percent Inhibition | Safening Effect (%) |
|---|---|---|---|---|---|---|
| | 2.24 | 2-methyl-allylcarbanilate | 4.48 | Wheat | 50 | 20 |
| | 0.28 | 2-methyl-allylcarbanilate | 4.48 | Sorghum | 25 | 25 |
| | 0.84 | 2-methyl-allylcarbanilate | 4.48 | Sorghum | 45 | 50 |
| | 2.24 | 2-methyl-allylcarbanilate | 4.48 | Sorghum | 70 | 24 |
| 43 | 2.24 | Allyl-N-methylcarbanilate | 4.48 | Wheat | 30 | 40 |
| | 0.28 | Allyl-N-methylcarbanilate | 4.48 | Sorghum | 15 | 35 |
| | 0.84 | Allyl-N-methylcarbanilate | 4.48 | Sorghum | 65 | 30 |
| | 2.24 | Allyl-N-methylcarbanilate | 4.48 | Sorghum | 85 | 9 |
| 44 | 0.84 | Pentyl-3,4-dichlorothionocarbanilate | 4.48 | Wheat | 0 | 5 |
| | 2.24 | Pentyl-3,4-dichlorothionocarbanilate | 4.48 | Wheat | 0 | 20 |
| 45 | 0.28 | Ethyl-3,4-dichlorothiolcarbanilate | 4.48 | Sorghum | 35 | 54 |
| 46 | 0.28 | Methyl-p-chlorothionocarbanilate | 2.24 | Wheat | 0 | 5 |
| | 0.84 | Methyl-p-chlorothionocarbanilate | 2.24 | Wheat | 0 | 5 |
| | 2.24 | Methyl-p-chlorothionocarbanilate | 2.24 | Wheat | 0 | 20 |
| 47 | 0.28 | 2-chloro-allyl-p-methyl-thiolcarbanilate | 4.48 | Sorghum | 60 | 29 |
| 48 | 0.28 | 2-chloro-allyl-N-methyl-dithiocarbanilate | 4.48 | Sorghum | 30 | 59 |
| | 0.84 | 2-chloro-allyl-N-methyl-dithiocarbanilate | 4.48 | Sorghum | 35 | 53 |
| | 2.24 | 2-chloro-allyl-N-methyl-dithiocarbanilate | 4.48 | Sorghum | 60 | 37 |
| 49 | 0.28 | Hexyl-m-methylcarbanilate | 4.48 | Sorghum | 65 | 24 |
| 50 | 0.28 | 2-chloro-allyl-N-propyldithiocarbanilate | 4.48 | Sorghum | 60 | 29 |
| 51 | 0.28 | 2-chloro-allyl-N-isopropyldithiocarbanilate | 4.48 | Sorghum | 30 | 59 |
| 52 | 0.28 | Allyl-N-methyldithiocarbanilate | 4.48 | Sorghum | 10 | 79 |
| | 0.84 | Allyl-N-methyldithiocarbanilate | 4.48 | Sorghum | 15 | 73 |
| | 2.24 | Allyl-N-methyldithiocarbanilate | 4.48 | Sorghum | 30 | 67 |
| 53 | 0.28 | Butyl-3,4-dichlorothiolcarbanilate | 4.48 | Sorghum | 50 | 29 |
| 54 | 0.28 | Allyl-N-ethyldithiocarbanilate | 4.48 | Sorghum | 50 | 20 |
| | 0.84 | Allyl-N-ethyldithio- | 4.48 | Sorghum | 75 | 23 |

TABLE I (A)-continued

| Example No. | Amount of alachlor Herbicide (kg./ha.) | Antagonistic Agent | Amount (kg./ha.) | Crop | Percent Inhibition | Safening Effect (%) |
|---|---|---|---|---|---|---|
| 55 | 0.28 | carbanilate 2-chloro-ethyl-N-methylthiono-carbanilate | 4.48 | Sorghum | 40 | 15 |
| 56 | 0.28 | 2-chloro-allyl-o-chloro-N-(2-chloroallyl)dithiocarbanilate | 4.48 | Wheat | 0 | 80 |
|  | 0.28 | 2-chloro-allyl-o-chloro-N-(2-chloroallyl)dithiocarbanilate | 4.48 | Sorghum | 15 | 40 |
|  | 0.84 | 2-chloro-allyl-o-chloro-N-(2-chloroallyl)dithiocarbanilate | 4.48 | Sorghum | 50 | 35 |
| 57 | 0.84 | Ethyl-N-(2-carbamoylethyl)-thiolcarbanilate | 4.48 | Sorghum | 60 | 25 |
|  | 2.24 | Ethyl-N-(2-carbamoylethyl)-thiolcarbanilate | 4.48 | Sorghum | 70 | 28 |
| 58 | 0.28 | Allyldithiocarbanilate | 4.48 | Wheat | 20 | 18 |
|  | 0.28 | Allyldithiocarbanilate | 4.48 | Sorghum | 50 | 10 |
|  | 0.84 | Allyldithiocarbanilate | 4.48 | Sorghum | 65 | 23 |
| 59 | 0.28 | Methyl-p-t-butyl-thionocarbanilate | 4.48 | Wheat | 20 | 18 |
|  | 0.28 | Methyl-p-t-butyl-thionocarbanilate | 4.48 | Sorghum | 25 | 35 |
|  | 0.84 | Methyl-p-t-butyl-thionocarbanilate | 4.48 | Sorghum | 55 | 33 |
|  | 2.24 | Methyl-p-t-butyl-thionocarbanilate | 4.48 | Sorghum | 85 | 8 |
| 60 | 0.28 | Ethyl-3-hydroxy-N-isopropyl-thiolcarbanilate | 4.48 | Wheat | 20 | 18 |
|  | 0.28 | Ethyl-3-hydroxy-N-isopropyl-thiolcarbanilate | 4.48 | Sorghum | 45 | 15 |
|  | 0.84 | Ethyl-3-hydroxy-N-isopropyl-thiolcarbanilate | 4.48 | Sorghum | 75 | 13 |
| 61 | 0.28 | Isopropyl-N-butyl-carbanilate | 4.48 | Sorghum | 40 | 30 |
|  | 0.56 | Isopropyl-N-butyl-carbanilate | 4.48 | Sorghum | 55 | 33 |
|  | 1.12 | Isopropyl-N-butyl-carbanilate | 4.48 | Sorghum | 55 | 38 |
|  | 2.24 | Isopropyl-N-butyl-carbanilate | 4.48 | Sorghum | 55 | 43 |
| 62 | 0.28 | Methyl-N-ethyldithiocarbanilate | 4.48 | Sorghum | 50 | 20 |
|  | 0.56 | Methyl-N-ethyldithiocarbanilate | 4.48 | Sorghum | 50 | 38 |
|  | 1.12 | Methyl-N-ethyldithiocarbanilate | 4.48 | Sorghum | 70 | 23 |
|  | 2.24 | Methyl-N-ethyldithiocarbanilate | 4.48 | Sorghum | 90 | 8 |

TABLE I (A)-continued

| Example No. | Amount of alachlor Herbicide (kg./ha.) | Antagonistic Agent | Amount (kg./ha.) | Crop | Percent Inhibition | Safening Effect (%) |
|---|---|---|---|---|---|---|
| 63 | 0.28 | Isobutyl-carbanilate | 4.48 | Sorghum | 30 | 40 |
|  | 0.56 | Isobutyl-carbanilate | 4.48 | Sorghum | 70 | 18 |
|  | 1.12 | Isobutyl-carbanilate | 4.48 | Sorghum | 70 | 23 |
|  | 2.24 | Isobutyl-carbanilate | 4.48 | Sorghum | 70 | 28 |
| 64 | 0.28 | t-butyl-carbanilate | 4.48 | Sorghum | 55 | 15 |
|  | 0.56 | t-butyl-carbanilate | 4.48 | Sorghum | 75 | 13 |
|  | 1.12 | t-butyl-carbanilate | 4.48 | Sorghum | 80 | 13 |
|  | 2.24 | t-butyl-carbanilate | 4.48 | Sorghum | 85 | 13 |
| 65 | 0.28 | Ethyl-N-ethyldithio-carbanilate | 4.48 | Sorghum | 45 | 25 |
|  | 0.56 | Ethyl-N-ethyldithio-carbanilate | 4.48 | Sorghum | 60 | 28 |
|  | 1.12 | Ethyl-N-ethyldithio-carbanilate | 4.48 | Sorghum | 70 | 23 |
|  | 2.24 | Ethyl-N-ethyldithio-carbanilate | 4.48 | Sorghum | 70 | 28 |
| 66 | 0.56 | t-butyl-N-isopropyl-thiolcarbanilate | 4.48 | Sorghum | 50 | 38 |
|  | 1.12 | t-butyl-N-isopropyl-thiolcarbanilate | 4.48 | Sorghum | 65 | 28 |
| 67 | 0.28 | Allyl-thionocarbanilate | 4.48 | Sorghum | 45 | 25 |
|  | 0.56 | Allyl-thionocarbanilate | 4.48 | Sorghum | 65 | 23 |
|  | 1.12 | Allyl-thionocarbanilate | 4.48 | Sorghum | 65 | 28 |
|  | 2.24 | Allyl-thionocarbanilate | 4.48 | Sorghum | 75 | 23 |
| 68 | 0.28 | 2-methyl-allylcarbanilate | 4.48 | Sorghum | 50 | 20 |
|  | 0.56 | 2-methyl-allylcarbanilate | 4.48 | Sorghum | 65 | 23 |
|  | 1.12 | 2-methyl-allylcarbanilate | 4.48 | Sorghum | 60 | 33 |
|  | 2.24 | 2-methyl-allylcarbanilate | 4.48 | Sorghum | 70 | 28 |
| 69 | 0.28 | Allyl-N-methyldithiocarbanilate | 2.24 | Sorghum | 35 | 35 |
|  | 0.28 | Allyl-N-methyldithiocarbanilate | 4.48 | Sorghum | 30 | 40 |
|  | 0.56 | Allyl-N-methyldithiocarbanilate | 2.24 | Sorghum | 55 | 33 |
|  | 0.56 | Allyl-N-methyldithiocarbanilate | 4.48 | Sorghum | 35 | 53 |
|  | 1.12 | Allyl-N-methyldithiocarbanilate | 2.24 | Sorghum | 60 | 33 |
|  | 1.12 | Allyl-N-methyldithiocarbanilate | 4.48 | Sorghum | 45 | 48 |
|  | 2.24 | Allyl-N-methyldithiocarbanilate | 2.24 | Sorghum | 80 | 18 |

TABLE I (A)-continued

| Example No. | Amount of alachlor Herbicide (kg./ha.) | Antagonistic Agent | Amount (kg./ha.) | Crop | Percent Inhibition | Safening Effect (%) |
|---|---|---|---|---|---|---|
| | 2.24 | Allyl-N-methyldithiocarbanilate | 4.48 | Sorghum | 55 | 43 |
| 70 | 0.28 | Ethyl-3,4-dichlorothiolcarbanilate | 4.48 | Sorghum | 55 | 15 |
| | 0.56 | Ethyl-3,4-dichlorothiolcarbanilate | 4.48 | Sorghum | 65 | 23 |
| 71 | 0.28 | 2-chloroallyl-N-methyldithiocarbanilate | 4.48 | Sorghum | 45 | 25 |
| | 0.56 | 2-chloroallyl-N-methyldithiocarbanilate | 4.48 | Sorghum | 60 | 28 |
| | 1.12 | 2-chloroallyl-N-methyldithiocarbanilate | 4.48 | Sorghum | 70 | 23 |
| | 2.24 | 2-chloroallyl-N-methyldithiocarbanilate | 4.48 | Sorghum | 80 | 18 |
| 72 | 0.28 | 2-chloroallyl-o-chloro-N-(2-chloroallyl)dithiocarbanilate | 4.48 | Sorghum | 50 | 20 |
| | 0.56 | 2-chloroallyl-o-chloro-N-(2-chloroallyl)dithiocarbanilate | 4.48 | Sorghum | 70 | 18 |
| 73 | 0.28 | Methyl-p-t-butyl-thionocarbanilate | 4.48 | Sorghum | 35 | 35 |
| | 0.56 | Methyl-p-t-butyl-thionocarbanilate | 4.48 | Sorghum | 60 | 28 |
| | 1.12 | Methyl-p-t-butyl-thionocarbanilate | 4.48 | Sorghum | 70 | 23 |
| | 2.24 | Methyl-p-t-butyl-thionocarbanilate | 4.48 | Sorghum | 75 | 23 |
| 74 | 0.28 | Cyclohexyl-N-allyl-cyclohexanecarbamate | 4.48 | Sorghum | 50 | 49 |
| 75 | 2.24 | Cyclohexyldiethyldithiocarbamate | 4.48 | Wheat | 60 | 20 |
| 76 | 0.28 | Isopropyl-N-ethylcyclohexanecarbamate | 4.48 | Wheat | 60 | 20 |
| | 2.24 | Isopropyl-N-ethylcyclohexanecarbamate | 4.48 | Sorghum | 75 | 24 |
| 77 | 0.28 | Methyl-N-isopropyldithiocyclohexanecarbamate | 4.48 | Sorghum | 60 | 39 |
| 78 | 2.24 | Methyl-N-methylthionocyclohexanecarbamate | 4.48 | Wheat | 50 | 30 |
| | 0.28 | Methyl-N-methylthionocyclohexanecarbamate | 4.48 | Sorghum | 80 | 19 |

TABLE I (A)-continued

| Example No. | Amount of alachlor Herbicide (kg./ha.) | Antagonistic Agent | Amount (kg./ha.) | Crop | Percent Inhibition | Safening Effect (%) |
|---|---|---|---|---|---|---|
| 79 | 0.28 | Ethyl-N-methylthionocyclohexane-carbamate | 4.48 | Sorghum | 75 | 24 |
| 80 | 0.28 | Ethyl-N-ethylthionocyclohexane-carbamate | 4.48 | Sorghum | 60 | 39 |
| 81 | 2.24 | Propyl-N-butylthionocyclohexane-carbamate | 4.48 | Wheat | 40 | 40 |
| 82 | 0.28 | Phenyldiethyldithio-carbamate | 4.48 | Sorghum | 65 | 33 |
| 83 | 0.28 | Ethyl-pyrrolidine-thionocarboxylate | 4.48 | Sorghum | 75 | 23 |
| 84 | 0.28 | 2-chloro-allyl-3,6-dihydro-1(2H)pyridinecarbodithioate | 4.48 | Sorghum | 75 | 22 |
|  | 2.24 | 2-chloro-allyl-3,6-dihydro-1(2H)pyridinecarbodithioate | 4.48 | Sorghum | 70 | 30 |
| 85 | 0.28 | 2-chloro-allyl-3,6-dihydro-1(2H)pyridinecarbothiolate | 4.48 | Sorghum | 75 | 22 |
|  | 2.24 | 2-chloro-allyl-3,6-dihydro-1(2H)pyridinecarbothiolate | 4.48 | Sorghum | 65 | 35 |
| 86 | 0.28 | 2-hydroxy-ethyl-5-ethyl-2-methyl-1-piperidinecarbodithioate | 4.48 | Sorghum | 75 | 22 |
| 87 | 0.28 | Ethyl-piperidinethio-carboxylate | 4.48 | Wheat | 10 | 15 |
|  | 2.24 | Ethyl-piperidinethio-carboxylate | 4.48 | Wheat | 60 | 20 |
|  | 0.28 | Ethyl-piperidinethio-carboxylate | 4.48 | Sorghum | 80 | 17 |
| 88 | 2.24 | 2-cyclo-hexen-1-yldiiso-propylthiolcarbamate | 4.48 | Wheat | 35 | 25 |
| 89 | 0.28 | Allyldithio-2-cyclohexene-1-carbamate | 4.48 | Wheat | 0 | 10 |
|  | 2.24 | Allyldithio-2-cyclohexene-1-carbamate | 4.48 | Wheat | 35 | 25 |
| 90 | 0.28 | Methyl-N-isopropyl-thiol-2-cyclo-hexene-1-carbamate | 4.48 | Sorghum | 60 | 35 |
| 91 | 0.28 | Ethyl-4-morpholine-carbothionate | 4.48 | Wheat | 20 | 30 |
|  | 2.24 | Ethyl-4-morpholine-carbothionate | 4.48 | Wheat | 75 | 23 |
| 92 | 0.28 | 3-chloro-2-butyl-4-morpholine-carbodithioate | 4.48 | Wheat | 25 | 25 |
|  | 2.24 | 3-chloro-2-butyl-4-morpholine-cardodithioate | 4.48 | Wheat | 80 | 8 |
| 93 | 0.28 | Allyl-4-morpholinecarbothionate | 4.48 | Wheat | 20 | 30 |
|  | 2.24 | Allyl-4-morpholinecarbothionate | 4.48 | Wheat | 80 | 8 |

TABLE I (A)-continued

| Example No. | Amount of alachlor Herbicide (kg./ha.) | Antagonistic Agent | Amount (kg./ha.) | Crop | Percent Inhibition | Safening Effect (%) |
|---|---|---|---|---|---|---|
| 94 | 0.28 | 2-chloro-allyl-2,6-dimethyl-4-morpholinecarbodithioate | 4.48 | Wheat | 30 | 20 |
|  | 0.28 | 2-chloro-allyl-2,6-dimethyl-4-morpholinecarbodithioate | 4.48 | Sorghum | 75 | 22 |
| 95 | 0.28 | Ethylhexahydro(1H)azepine-1-carbothionate | 4.48 | Wheat | 20 | 30 |
|  | 2.24 | Ethylhexahydro(1H)azepine-1-carbothionate | 4.48 | Wheat | 75 | 13 |
| 96 | 0.28 | Methylhexahydro(1H)azepine-1-carboxylate | 4.48 | Wheat | 25 | 25 |
| 97 | 0.28 | Pentylhexahydro(1H)azepine-1-carboxylate | 4.48 | Wheat | 15 | 35 |
|  | 2.24 | Pentylhexahydro(1H)azepine-1-carboxylate | 4.48 | Wheat | 70 | 18 |
|  | 0.28 | Pentylhexahydro(1H)azepine-1-carboxylate | 4.48 | Sorghum | 70 | 27 |
| 98 | 0.28 | Isopropyl-hexahydro(1H)azepine-1-carboxylate | 4.48 | Wheat | 20 | 30 |
|  | 2.24 | Isopropyl-hexahydro(1H)azepine-1-carboxylate | 4.48 | Wheat | 80 | 8 |
| 99 | 0.28 | Octyloctahydro(1H)azonine-1-carbothiolate | 1.12 | Wheat | 30 | 20 |
|  | 2.24 | Octyloctahydro(1H)azonine-1-carbothiolate | 1.12 | Wheat | 75 | 13 |
| 100 | 0.28 | Isopropyl-hexahydroazocine-1(2H)azoninethionocarboxylate | 4.48 | Wheat | 30 | 20 |
|  | 2.24 | Isopropyl-hexahydroazocine-1(2H)azoninethionocarboxylate | 4.48 | Wheat | 65 | 23 |
| 101 | 0.28 | Ethyloctahydro(1H)azonine-thionocarboxylate | 4.48 | Wheat | 20 | 30 |
|  | 2.24 | Ethyloctahydro(1H)azonine-thionocarboxylate | 4.48 | Wheat | 60 | 28 |
| 102 | 0.07 | Allyl-N-methyldithiocarbanilate | 4.48 | Wheat | 0 | 10 |
|  | 0.28 | Allyl-N-methyldithiocarbanilate | 4.48 | Wheat | 15 | 23 |
|  | 1.12 | Allyl-N-methyldithiocarbanilate | 4.48 | Wheat | 35 | 40 |
|  | 0.07 | Allyl-N-methyldithiocarbanilate | 4.48 | Sorghum | 15 | 35 |
|  | 0.28 | Allyl-N-methyldithiocarbanilate | 4.48 | Sorghum | 40 | 58 |
|  | 1.12 | Allyl-N-methyldithiocarbanilate | 4.48 | Sorghum | 80 | 20 |
| 103 | 0.07 | Methyl-N-methyldithiocarbanilate | 4.48 | Wheat | 0 | 10 |
|  | 0.28 | Methyl-N-methyldithiocarbanilate | 4.48 | Wheat | 0 | 38 |

TABLE I (A)-continued

| Example No. | Amount of alachlor Herbicide (kg./ha.) | Antagonistic Agent | Amount (kg./ha.) | Crop | Percent Inhibition | Safening Effect (%) |
|---|---|---|---|---|---|---|
| | 1.12 | Methyl-N-methyldithiocarbanilate | 4.48 | Wheat | 20 | 55 |
| | 4.48 | Methyl-N-methyldithiocarbanilate | 4.48 | Wheat | 40 | 50 |
| | 0.07 | Methyl-N-methyldithiocarbanilate | 4.48 | Sorghum | 20 | 30 |
| | 0.28 | Methyl-N-methyldithiocarbanilate | 4.48 | Sorghum | 50 | 48 |
| | 1.12 | Methyl-N-methyldithiocarbanilate | 4.48 | Sorghum | 85 | 15 |
| 104 | 0.07 | Butyl-N-methylcarbanilate | 4.48 | Wheat | 0 | 10 |
| | 0.28 | Butyl-N-methylcarbanilate | 4.48 | Wheat | 15 | 23 |
| | 1.12 | Butyl-N-methylcarbanilate | 4.48 | Wheat | 40 | 35 |
| | 0.07 | Butyl-N-methylcarbanilate | 4.48 | Sorghum | 25 | 25 |
| | 0.28 | Butyl-N-methylcarbanilate | 4.48 | Sorghum | 75 | 23 |
| 105 | 0.14 | 2-chloroallyl-3,4-dichloro-N-(2-chloroallyl)dithiocarbanilate | 4.48 | Wheat | 0 | 20 |
| | 0.84 | 2-chloroallyl-3,4-dichloro-N-(2-chloroallyl)dithiocarbanilate | 4.48 | Wheat | 45 | 40 |
| | 0.14 | 2-chloroallyl-3,4-dichloro-N-(2-chloroallyl)dithiocarbanilate | 4.48 | Sorghum | 50 | 40 |
| 106 | 0.14 | 2-chloroallyl-N-allyl-3,4-dichlorodithiocarbanilate | 4.48 | Sorghum | 50 | 40 |
| 107 | 0.14 | Methyl-N-allyl-3,4-dichlorodithiocarbanilate | 4.48 | Wheat | 0 | 20 |
| | 0.14 | Methyl-N-allyl-3,4-dichlorodithiocarbanilate | 4.48 | Sorghum | 65 | 25 |
| 108 | 0.14 | Allyl-3,4-dichloro-N-(2-chloroallyl)dithiocarbanilate | 4.48 | Wheat | 10 | 10 |
| | 0.84 | Allyl-3,4-dichloro-N-(2-chloroallyl)dithiocarbanilate | 4.48 | Wheat | 70 | 15 |
| | 0.14 | Allyl-3,4-dichloro-N-(2-chloroallyl)dithiocarbanilate | 4.48 | Sorghum | 65 | 25 |
| 109 | 0.14 | 2-chloroallyl-p-chloro-N-ethyldithiocarbanilate | 4.48 | Sorghum | 75 | 15 |
| 110 | 0.14 | 2,3,3-trichloroallyl-o-chlorocarbanilate | 4.48 | Sorghum | 60 | 30 |
| 111 | 0.14 | 2,3,3-trichloroallyl-p-chlorocarbanilate | 4.48 | Sorghum | 70 | 20 |
| 112 | 0.14 | 2-chloro-3- | 4.48 | Wheat | 10 | 50 |

TABLE I (A)-continued

| Example No. | Amount of alachlor Herbicide (kg./ha.) | Antagonistic Agent | Amount (kg./ha.) | Crop | Percent Inhibition | Safening Effect (%) |
|---|---|---|---|---|---|---|
| | 0.84 | butenyl-p-bromo-carbanilate 2-chloro-3-butenyl-p-bromo-carbanilate | 4.48 | Wheat | 70 | 24 |
| | 0.14 | 2-chloro-3-butenyl-p-bromo-carbanilate | 4.48 | Sorghum | 65 | 25 |
| 113 | 0.14 | Allyl-p-chlorodithiocarbanilate | 4.48 | Wheat | 35 | 25 |
| | 0.84 | Allyl-p-chlorodithiocarbanilate | 4.48 | Wheat | 70 | 24 |
| | 0.14 | Allyl-p-chlorodithiocarbanilate | 4.48 | Sorghum | 65 | 24 |
| 114 | 0.14 | 2-chloro-allyl-p-chlorodithiocarbanilate | 4.48 | Wheat | 0 | 60 |
| | 0.84 | 2-chloro-allyl-p-chlorodithiocarbanilate | 4.48 | Wheat | 55 | 39 |
| 115 | 0.14 | 2-chloro-allyl-3,4-dichlorodithiocarbanilate | 4.48 | Wheat | 25 | 35 |
| 116 | 0.14 | 2-chloro-allyl-p-nitro-dithiocarbanilate | 4.48 | Wheat | 30 | 30 |
| | 0.84 | 2-chloro-allyl-p-nitro-dithiocarbanilate | 4.48 | Wheat | 75 | 19 |
| 117 | 0.14 | 2-chloro-allyl-3-nitro-carbanilate | 4.48 | Wheat | 25 | 35 |
| 118 | 0.14 | 3-chloro-allyl-3-nitro-carbanilate | 4.48 | Wheat | 35 | 25 |
| | 0.14 | 3-chloro-allyl-3-nitro-carbanilate | 4.48 | Sorghum | 75 | 15 |
| 119 | 0.14 | 2-chloro-allyl-p-fluoro-dithiocarbanilate | 4.48 | Wheat | 10 | 50 |
| | 0.84 | 2-chloro-allyl-p-fluoro-dithiocarbanilate | 4.48 | Wheat | 70 | 24 |
| 120 | 0.14 | 4-iodo-2-butynyl-p-methoxycarbanilate | 4.48 | Wheat | 15 | 35 |
| | 0.84 | 4-iodo-2-butynyl-p-methoxycarbanilate | 4.48 | Wheat | 50 | 44 |
| | 4.48 | 4-iodo-2-butynyl-p-methoxycarbanilate | 4.48 | Wheat | 75 | 20 |
| | 0.14 | 4-iodo-2-butynyl-p-methoxycarbanilate | 4.48 | Sorghum | 75 | 15 |
| 121 | 0.07 | Allyl-N-methyldithio-carbanilate | 4.48 | Wheat | 0 | 30 |
| | 0.28 | Allyl-N-methyldithio-carbanilate | 4.48 | Wheat | 10 | 25 |
| | 1.12 | Allyl-N-methyldithio-carbanilate | 4.48 | Wheat | 30 | 35 |
| | 0.07 | Allyl-N-methyldithio-carbanilate | 4.48 | Sorghum | 15 | 80 |
| | 0.28 | Allyl-N-methyldithio-carbanilate | 4.48 | Sorghum | 30 | 65 |
| | 1.12 | Allyl-N-methyldithio- | 4.48 | Sorghum | 50 | 49 |

TABLE I (A)-continued

| Example No. | Amount of alachlor Herbicide (kg./ha.) | Antagonistic Agent | Amount (kg./ha.) | Crop | Percent Inhibition | Safening Effect (%) |
|---|---|---|---|---|---|---|
| | 4.48 | carbanilate Allyl-N-methyldithio-carbanilate | 4.48 | Sorghum | 75 | 24 |
| 122 | 0.07 | Benzyldiisopropylcarbamate | 4.48 | Wheat | 0 | 30 |
| | 0.28 | Benzyldiisopropylcarbamate | 4.48 | Wheat | 20 | 15 |
| | 1.12 | Benzyldiisopropylcarbamate | 4.48 | Wheat | 35 | 30 |
| | 4.48 | Benzyldiisopropylcarbamate | 4.48 | Wheat | 80 | 18 |
| | 0.07 | Benzyldiisopropylcarbamate | 4.48 | Sorghum | 20 | 75 |
| | 0.28 | Benzyldiisopropylcarbamate | 4.48 | Sorghum | 40 | 55 |
| | 1.12 | Benzyldiisopropylcarbamate | 4.48 | Sorghum | 65 | 34 |
| 123 | 0.07 | Benzylisobutyldithiocarbamate | 2.24 | Wheat | 0 | 30 |
| | 0.28 | Benzylisobutyldithiocarbamate | 2.24 | Wheat | 10 | 25 |
| | 1.12 | Benzylisobutyldithiocarbamate | 2.24 | Wheat | 45 | 20 |
| | 4.48 | Benzylisobutyldithiocarbamate | 2.24 | Wheat | 75 | 23 |
| | 0.07 | Benzylisobutyldithiocarbamate | 2.24 | Sorghum | 55 | 40 |
| | 0.28 | Benzylisobutyldithiocarbamate | 2.24 | Sorghum | 70 | 25 |
| 124 | 0.07 | Cyclohexyl-N-allyl-cyclohexanecarbamate | 4.48 | Wheat | 0 | 30 |
| | 0.28 | Cyclohexyl-N-allyl-cyclohexanecarbamate | 4.48 | Wheat | 15 | 20 |
| | 0.07 | Cyclohexyl-N-allyl-cyclohexanecarbamate | 4.48 | Sorghum | 30 | 65 |
| | 0.28 | Cyclohexyl-N-allyl-cyclohexanecarbamate | 4.48 | Sorghum | 70 | 25 |
| 125 | 0.07 | Ethyl-N-ethylthionocyclohexanecarbamate | 2.24 | Wheat | 0 | 30 |
| | 0.28 | Ethyl-N-ethylthionocyclohexanecarbamate | 2.24 | Wheat | 10 | 25 |
| | 0.07 | Ethyl-N-ethylthionocyclohexanecarbamate | 2.24 | Sorghum | 30 | 65 |
| | 0.28 | Ethyl-N-ethylthionocyclohexanecarbamate | 2.24 | Sorghum | 70 | 25 |
| 126 | 0.07 | Ethylthiol-cyclohexanecarbamate | 4.48 | Wheat | 0 | 30 |
| | 0.07 | Ethylthiol-cyclohexanecarbamate | 4.48 | Sorghum | 40 | 55 |
| 127 | 0.07 | Propyl-N-butylthionocyclohexanecarbamate | 4.48 | Wheat | 0 | 30 |
| | 0.28 | Propyl-N-butylthionocyclohexane- | 4.48 | Wheat | 15 | 20 |

TABLE I (A)-continued

| Example No. | Amount of alachlor Herbicide (kg./ha.) | Antagonistic Agent | Amount (kg./ha.) | Crop | Percent Inhibition | Safening Effect (%) |
|---|---|---|---|---|---|---|
| | 0.07 | Propyl-N-butylthiono-cyclohexane-carbamate | 4.48 | Sorghum | 70 | 25 |
| 128 | 0.07 | Phenyldi-ethyldithio-carbamate | 4.48 | Wheat | 0 | 30 |
| | 0.28 | Phenyldi-ethyldithio-carbamate | 4.48 | Wheat | 10 | 25 |
| | 0.07 | Phenyldi-ethyldithio-carbamate | 4.48 | Sorghum | 0 | 95 |
| | 0.28 | Phenyldi-ethyldithio-carbamate | 4.48 | Sorghum | 40 | 55 |
| 129 | 0.07 | 2-chloro-allyl-3,6-dihydro-1(2H)pyridine carbothiolate | 4.48 | Wheat | 0 | 30 |
| | 0.07 | 2-chloro-allyl-3,6-dihydro-1(2H)pyridine carbothiolate | 4.48 | Sorghum | 60 | 35 |
| 130 | 0.07 | Ethyl-piperidinethio-carboxylate | 4.48 | Wheat | 0 | 30 |
| | 0.28 | Ethyl-piperidinethio-carboxylate | 4.48 | Wheat | 20 | 15 |
| | 1.12 | Ethyl-piperidinethio-carboxylate | 4.48 | Wheat | 45 | 20 |
| | 0.07 | Ethyl-piperidinethio-carboxylate | 4.48 | Sorghum | 75 | 20 |
| 131 | 0.28 | Allyl-N-methyldi-thiocar-banilate | 4.48 | Wheat | 0 | 25 |
| | 1.12 | Allyl-N-methyldi-thiocar-banilate | 4.48 | Wheat | 45 | 25 |
| | 0.07 | Allyl-N-methyldi-thiocar-banilate | 4.48 | Sorghum | 15 | 35 |
| | 0.28 | Allyl-N-methyldi-thiocar-banilate | 4.48 | Sorghum | 25 | 65 |
| | 1.12 | Allyl-N-methyldi-thiocar-banilate | 4.48 | Sorghum | 40 | 60 |
| | 4.48 | Allyl-N-methyldi-thiocar-banilate | 4.48 | Sorghum | 50 | 50 |
| 132 | 0.07 | Allyldi-thio-2-cyclo-hexene-1-carbamate | 4.48 | Sorghum | 25 | 25 |
| | 0.28 | Allyldi-thio-2-cyclo-hexene-1-carbamate | 4.48 | Sorghum | 50 | 40 |
| | 1.12 | Allyldi-thio-2-cyclo-hexene-1-carbamate | 4.48 | Sorghum | 80 | 20 |
| 133 | 0.28 | 2-cyclo-hexen-1-yl diisopropyl-thiolcarbamate | 4.48 | Wheat | 10 | 15 |
| | 1.12 | 2-cyclo-hexen-1-yl diisopropyl-thiolcarbamate | 4.48 | Wheat | 20 | 50 |
| 134 | 0.07 | Pentylhexa-hydro(1H)-azepine-1-carboxylate | 4.48 | Sorghum | 25 | 24 |
| | 0.28 | Pentylhexa-hydro(1H)-azepine-1-car- | 4.48 | Sorghum | 50 | 40 |

TABLE I (A)-continued

| Example No. | Amount of alachlor Herbicide (kg./ha.) | Antagonistic Agent | Amount (kg./ha.) | Crop | Percent Inhibition | Safening Effect (%) |
|---|---|---|---|---|---|---|
| | 1.12 | boxylate Pentylhexahydro(1H)-azepine-1-carboxylate | 4.48 | Sorghum | 85 | 15 |
| 135 | 0.28 | Isopropyl-hexahydroazocine-1(2H)carbothionate | 4.48 | Wheat | 0 | 25 |
| | 1.12 | Isopropyl-hexahydroazocine-1(2H)carbothionate | 4.48 | Wheat | 25 | 45 |
| | 4.48 | Isopropyl-hexahydroazocine-1(2H)carbothionate | 4.48 | Wheat | 75 | 15 |
| 136 | 0.28 | Ethyloctahydro(1H)azoninethionocarboxylate | 4.48 | Wheat | 0 | 25 |
| | 1.12 | Ethyloctahydro(1H)azoninethionocarboxylate | 4.48 | Wheat | 30 | 40 |
| 137 | 0.07 | Methyl-N-methyldithiocarbanilate | 4.48 | Sorghum | 40 | 10 |
| | 0.28 | Methyl-N-methyldithiocarbanilate | 4.48 | Sorghum | 45 | 45 |
| | 1.12 | Methyl-N-methyldithiocarbanilate | 4.48 | Sorghum | 65 | 35 |
| 138 | 0.28 | 3-chloro-2-butenyl-carbanilate | 4.48 | Wheat | 0 | 25 |
| | 1.12 | 3-chloro-2-butenyl-carbanilate | 4.48 | Wheat | 50 | 20 |
| | 0.07 | 3-chloro-2-butenyl-carbanilate | 4.48 | Sorghum | 30 | 20 |
| | 0.28 | 3-chloro-2-butenyl-carbanilate | 4.48 | Sorghum | 65 | 25 |
| | 1.12 | 3-chloro-2-butenyl-carbanilate | 4.48 | Sorghum | 70 | 30 |
| 139 | 0.14 | Allylthiolcarbamate | 4.48 | Wheat | 30 | 18 |
| | 0.14 | Allylthiolcarbamate | 4.48 | Sorghum | 65 | 32 |
| 140 | 0.14 | 2-nitro-4-trifluoromethylphenyl-N,N-dimethyldithiocarbamate | 4.48 | Sorghum | 50 | 47 |
| 141 | 0.14 | Allyl-N-cyclohexyl-thionocarbanilate | 4.48 | Wheat | 15 | 33 |
| | 0.84 | Allyl-N-cyclohexyl-thionocarbanilate | 4.48 | Wheat | 55 | 20 |
| | 0.14 | Allyl-N-cyclohexyl-thionocarbanilate | 4.48 | Sorghum | 35 | 62 |
| | 0.84 | Allyl-N-cyclohexyl-thionocarbanilate | 4.48 | Sorghum | 65 | 33 |
| 142 | 0.14 | Methyl-4-morpholinocarbodithioate | 4.48 | Wheat | 20 | 28 |
| 143 | 0.14 | Methyl-N-butylcarbanilate | 4.48 | Wheat | 15 | 33 |
| | 0.84 | Methyl-N-butylcarbanilate | 4.48 | Wheat | 50 | 25 |
| 144 | 0.14 | Allyl-N-methylthiolcarbamate | 4.48 | Wheat | 15 | 33 |
| | 0.14 | Allyl-N-methylthiolcarbamate | 4.48 | Sorghum | 50 | 47 |
| | 0.84 | Allyl-N-methylthiolcarbamate | 4.48 | Sorghum | 75 | 23 |
| 145 | 0.28 | 2-chloro- | 4.48 | Sorghum | 10 | 5 |

TABLE I (A)-continued

| Example No. | Amount of alachlor Herbicide (kg./ha.) | Antagonistic Agent | Amount (kg./ha.) | Crop | Percent Inhibition | Safening Effect (%) |
|---|---|---|---|---|---|---|
|  | 0.56 | allyl-N-isobutyldithiocarbanilate | 4.48 | Sorghum | 15 | 20 |
|  | 1.12 | 2-chloroallyl-N-isobutyldithiocarbanilate | 4.48 | Sorghum | 25 | 20 |
|  | 2.24 | 2-chloroallyl-N-isobutyldithiocarbanilate | 4.48 | Sorghum | 30 | 60 |
| 146 | 0.28 | 2-chloroallyl-p-chlorodithiocarbanilate | 4.48 | Sorghum | 10 | 5 |
|  | 0.56 | 2-chloroallyl-p-chlorodithiocarbanilate | 4.48 | Sorghum | 15 | 20 |
|  | 2.24 | 2-chloroallyl-p-chlorodithiocarbanilate | 4.48 | Sorghum | 55 | 35 |
| 147 | 0.56 | Methyl-p-methyl-N-methyl-dithiocarbanilate | 4.48 | Sorghum | 45 | 43 |
|  | 1.12 | Methyl-p-methyl-N-methyl-dithiocarbanilate | 4.48 | Sorghum | 45 | 45 |
|  | 2.24 | Methyl-p-methyl-N-methyl-dithiocarbanilate | 4.48 | Sorghum | 50 | 47 |
|  | 4.48 | Methyl-p-methyl-N-methyl-dithiocarbanilate | 4.48 | Sorghum | 55 | 42 |

TABLE I (B)

| Ex. No. | Acetanilide Herbicide | Amount (kg./ha.) | Antagonistic Agent | Amount (kg./ha.) | Crop | Percent Inhibition | Safening Effect (%) |
|---|---|---|---|---|---|---|---|
| 148 | alachlor | 4.48 | Methyl-N-methyl-O-methyldithiocarbanilate | 4.48 | Wheat | 35 | 43 |
|  | alachlor | 4.48 | Methyl-N-methyl-O-methyldithiocarbanilate | 4.48 | Sorghum | 75 | 20 |
|  | butachlor | 4.48 | Methyl-N-methyl-O-methyldithiocarbanilate | 4.48 | Wheat | 10 | 33 |
|  | butachlor | 4.48 | Methyl-N-methyl-O-methyldithiocarbanilate | 4.48 | Sorghum | 40 | 35 |
| 149 | butachlor | 4.48 | Methyl-N-ethyl-p-chloro-dithiocarbanilate | 4.48 | Wheat | 20 | 23 |
|  | butachlor | 4.48 | Methyl-N-ethyl-p-chloro-dithiocarbanilate | 4.48 | Sorghum | 45 | 30 |
| 150 | alachlor | 0.56 | 2-cyclohexen-1-yl-N-methyldithiocarbanilate | 4.48 | Sorghum | 50 | 33 |
|  | alachlor | 4.48 | 2-cyclohexen-1-yl-N-methyldithiocarbanilate | 4.48 | Sorghum | 70 | 25 |
|  | butachlor | 4.48 | 2-cyclohexen-1-yl-N-methyldithiocarbanilate | 4.48 | Sorghum | 50 | 25 |
| 151 | butachlor | 4.48 | Ethyl-N-isopropyl-carbanilate | 4.48 | Sorghum | 65 | 20 |
| 152 | butachlor | 0.56 | Isopropyl-N-isopropylcarbanilate | 4.48 | Sorghum | 15 | 25 |

TABLE I (B)-continued

| Ex. No. | Acetanilide Herbicide | Amount (kg./ha.) | Antagonistic Agent | Amount (kg./ha.) | Crop | Percent Inhibition | Safening Effect (%) |
|---|---|---|---|---|---|---|---|
| | butachlor | 4.48 | Isopropyl-N-isopropyl-carbanilate | 4.48 | Sorghum | 55 | 30 |
| 153 | butachlor | 4.48 | Methyl-N-isopropyl-carbanilate | 4.48 | Sorghum | 60 | 25 |
| 154 | butachlor | 4.48 | Butyl-N-isopropylthiol-carbanilate | 4.48 | Sorghum | 70 | 15 |
| 155 | butachlor | 4.48 | o-fluoro-benzyl-N-methyldithio-carbanilate | 4.48 | Sorghum | 60 | 25 |
| 156 | butachlor | 4.48 | m-fluoro-benzyl-N-methyldithio-carbanilate | 4.48 | Sorghum | 70 | 15 |
| 157 | butachlor | 4.48 | m-trifluoromethylbenzyl-N-methyldithio-carbanilate | 4.48 | Wheat | 10 | 35 |
| | butachlor | 0.56 | m-trifluoromethylbenzyl-N-methyldithio-carbanilate | 4.48 | Sorghum | 20 | 20 |
| | butachlor | 4.48 | m-trifluoromethylbenzyl-N-methyldithio-carbanilate | 4.48 | Sorghum | 60 | 25 |
| 158 | butachlor | 0.56 | Benzyl-N-butyldithio-carbanilate | 4.48 | Wheat | 0 | 15 |
| | butachlor | 0.56 | Benzyl-N-butyldithio-carbanilate | 4.48 | Sorghum | 20 | 20 |
| 159 | butachlor | 4.48 | Methyl-N-propyldithio-carbanilate | 4.48 | Wheat | 20 | 25 |
| | butachlor | 4.48 | Methyl-N-propyldithio-carbanilate | 4.48 | Sorghum | 45 | 40 |
| 160 | alachlor | 0.28 | Allyl-N-propyldithio-carbanilate | 4.48 | Sorghum | 35 | 20 |
| | butachlor | 0.56 | Allyl-N-propyldithio-carbanilate | 4.48 | Sorghum | 30 | 10 |
| | butachlor | 4.48 | Allyl-N-propyldithio-carbanilate | 4.48 | Sorghum | 45 | 40 |
| 161 | alachlor | 0.28 | Methyl-N-propylthiol-carbanilate | 4.48 | Sorghum | 45 | 10 |
| | alachlor | 2.24 | Methyl-N-propylthiol-carbanilate | 4.48 | Sorghum | 75 | 10 |
| | butachlor | 0.56 | Methyl-N-propylthiol-carbanilate | 4.48 | Sorghum | 25 | 15 |
| 162 | butachlor | 4.48 | Ethyl-N-propylthiol-carbanilate | 4.48 | Sorghum | 70 | 15 |
| 163 | butachlor | 4.48 | Propyl-N-propylthiol-carbanilate | 4.48 | Sorghum | 70 | 15 |
| 164 | butachlor | 4.48 | Propyl-N-propyldithio-carbanilate | 4.48 | Wheat | 25 | 20 |
| 165 | butachlor | 4.48 | Allylthiono-carbanilate | 4.48 | Sorghum | 55 | 40 |
| 166 | alachlor | 2.24 | Cyanoethyl-N-methyl-dithio-carbanilate | 4.48 | Sorghum | 45 | 25 |
| | butachlor | 4.48 | Cyanoethyl-N-methyl-dithio-carbanilate | 4.48 | Sorghum | 60 | 35 |
| 167 | butachlor | 4.48 | Butyl-N-isopropyl-dithio-carbanilate | 4.48 | Sorghum | 50 | 45 |
| 168 | butachlor | 0.56 | Methyl-N-isopropyl-dithio-carbanilate | 4.48 | Wheat | 0 | 10 |
| | butachlor | 4.48 | Methyl-N-isopropyl- | 4.48 | Wheat | 20 | 25 |

TABLE I (B)-continued

| Ex. No. | Acetanilide Herbicide | Amount (kg./ha.) | Antagonistic Agent | Amount (kg./ha.) | Crop | Percent Inhibition | Safening Effect (%) |
|---|---|---|---|---|---|---|---|
| 169 | butachlor | 4.48 | Butyl-N-isopropyl-dithio-carbanilate | 4.48 | Sorghum | 70 | 25 |
| 170 | butachlor | 4.48 | Propyl-N-isopropyl-carbanilate | 4.48 | Sorghum | 70 | 25 |
| 171 | butachlor | 4.48 | Allyl-m-chlorodithio-carbanilate | 4.48 | Sorghum | 65 | 23 |
| 172 | butachlor | 0.56 | 2-chloro-allyldithio-carbanilate | 4.48 | Sorghum | 20 | 20 |
| 173 | alachlor | 0.28 | Allylthiono-carbanilate | 4.48 | Wheat | 20 | 35 |
|  | butachlor | 0.56 | Allylthiono-carbanilate | 4.48 | Sorghum | 45 | 38 |
|  | butachlor | 2.24 | Allylthiono-carbanilate | 4.48 | Sorghum | 60 | 33 |
|  | butachlor | 8.96 | Allylthiono-carbanilate | 4.48 | Sorghum | 70 | 28 |
| 174 | butachlor | 0.56 | Isopropyl-N-butyl-carbanilate | 4.48 | Sorghum | 50 | 33 |
|  | butachlor | 2.24 | Isopropyl-N-butyl-carbanilate | 4.48 | Sorghum | 70 | 23 |
| 175 | alachlor | 0.56 | Allyl-N-methyldithio-carbanilate | 4.48 | Sorghum | 60 | 25 |
|  | alachlor | 1.12 | Allyl-N-methyldithio-carbanilate | 4.48 | Sorghum | 75 | 20 |
|  | butachlor | 0.56 | Allyl-N-methyldithio-carbanilate | 4.48 | Sorghum | 20 | 63 |
|  | butachlor | 2.24 | Allyl-N-methyldithio-carbanilate | 4.48 | Sorghum | 50 | 43 |
|  | butachlor | 8.96 | Allyl-N-methyldithio-carbanilate | 4.48 | Sorghum | 60 | 38 |
| 176 | alachlor | 0.28 | Methyl-N-ethyldithio-carbanilate | 4.48 | Wheat | 0 | 55 |
|  | alachlor | 1.12 | Methyl-N-ethyldithio-carbanilate | 4.48 | Wheat | 45 | 48 |
|  | alachlor | 4.48 | Methyl-N-ethyldithio-carbanilate | 4.48 | Wheat | 70 | 30 |
|  | alachlor | 0.28 | Methyl-N-ethyldithio-carbanilate | 4.48 | Sorghum | 60 | 33 |
|  | butachlor | 0.56 | Methyl-N-ethyldithio-carbanilate | 4.48 | Sorghum | 50 | 33 |
|  | butachlor | 2.24 | Methyl-N-ethyldithio-carbanilate | 4.48 | Sorghum | 70 | 23 |
| 177 | 2'-t-butyl-6'-methyl-2-bromo-acetanilide | 4.48 | Allylthiono-carbanilate | 4.48 | Wheat | 40 | 40 |
|  | N-butoxymethyl-2'-t-butyl-6'-methyl-acetanilide | 0.28 | Allylthiono-carbanilate | 4.48 | Wheat | 40 | 33 |
| 178 | 2'-t-butyl-6'-methyl-2-bromo-acetanilide | 1.12 | Isopropyl-N-butyl-carbanilate | 4.48 | Wheat | 35 | 25 |
|  | 2'-t-butyl-6'-methyl-2-bromo-acetanilide | 0.28 | Isopropyl-N-butyl carbanilate | 4.48 | Sorghum | 30 | 67 |
| 179 | 2'-t-butyl-6'-methyl-2-bromo-acetanilide | 0.28 | Allyl-N-methyldithio-carbanilate | 4.48 | Wheat | 70 | 27 |
|  | N-butoxymethyl-2'-t-butyl-6'-methyl-acetanilide | 0.28 | Allyl-N-methyldithio-carbanilate | 4.48 | Wheat | 40 | 33 |
|  | N-butoxy- | 0.28 | Allyl-N- | 4.48 | Sorghum | 35 | 63 |

TABLE I (B)-continued

| Ex. No. | Acetanilide Herbicide | Amount (kg./ha.) | Antagonistic Agent | Amount (kg./ha.) | Crop | Percent Inhibition | Safening Effect (%) |
|---|---|---|---|---|---|---|---|
| | methyl-2'-t-butyl-6'-methyl-acetanilide | | methyldithio-carbanilate | | | | |
| 180 | 2'-t-butyl-6'-methyl-2-bromo-acetanilide | 0.28 | Methyl-N-ethyldithio-carbanilate | 4.48 | Wheat | 0 | 10 |
| | 2'-t-butyl-6'-methyl-2-bromo-acetanilide | 1.12 | Methyl-N-ethyldithio-carbanilate | 4.48 | Wheat | 30 | 30 |
| | N-butoxymethyl-2'-t-butyl-6'-methyl-acetanilide | 0.28 | Methyl-N-ethyldithio-carbanilate | 4.48 | Wheat | 40 | 33 |
| | N-butoxymethyl-2'-t-butyl-6'-methyl-acetanilide | 1.12 | Methyl-N-ethyldithio-carbanilate | 4.48 | Wheat | 65 | 28 |
| | N-butoxymethyl-2'-t-butyl-6'-methyl-acetanilide | 0.28 | Methyl-N-ethyldithio-carbanilate | 4.48 | Sorghum | 70 | 28 |

In the tables herein, the columns headed Percent Inhibition contain the observations of test pans of plants which quantify the response of plants to a combination treatment of acentanilide herbicide and safening agent. Likewise, the columns headed Safening Effect (%) contain the difference between the response of plants to treatment with acetanilide herbicide and the response of plants to a combination treatment of the same acetanilide herbicide and safening agent. Although in the foregoing examples the safening agent is applied to the soil before the acetanilide herbicide, equivalent results are obtainable when the safening agent is applied in mixture with the acetanilide herbicide or in sequence after the acetanilide herbicide is applied. This also is observed in post-emergent applications. The ability to be applied as mixtures and obtain safening of acetanilide herbicide with wheat and sorghum is confirmed in tank mix tests.

A key contribution of the present invention is that the safening or antagonistic agents when applied to seed reduce crop injury without reducing effective weed control by the acetanilide herbicides.

EXAMPLE 181

The procedure employed in Examples 1 through 180 is repeated except that neither the herbicide nor the antagonistic agents are incorporated into the soil, but rather the soil is placed over sorghum and weed seeds, the herbicide is sprayed on the surface of the soil, the antagonistic agent is then sprayed on the surface of the soil and then water from overhead is added to a depth of 6.3 mm. across the surface of each pan. Thereafter, until observation of results, water is added from below by subirrigation. All weeds are substantially controlled. The safening effect on sorghum is shown in Table II.

TABLE II

| Amount of alachlor Herbicide (kg./ha.) | Antagonistic Agent | Amount (kg./ha.) | Percent Inhibition | Safening Effect(%) |
|---|---|---|---|---|
| 0.28 | Isopropyl-N-butylcarbanilate | 4.48 | 30 | 60 |
| 0.56 | Isopropyl-N-butylcarbanilate | 4.48 | 20 | 75 |
| 1.12 | Isopropyl N-butylcarbanilate | 4.48 | 85 | 12 |
| 2.24 | Isopropyl N-butylcarbanilate | 4.48 | 70 | 29 |
| 0.28 | Methyl-N-ethyldithio-carbanilate | 4.48 | 30 | 60 |
| 0.56 | Methyl-N-ethyldithio-carbanilate | 4.48 | 55 | 40 |
| 1.12 | Methyl-N-ethyldithio-carbanilate | 4.48 | 80 | 17 |
| 2.24 | Methyl-N-ethyldithio-carbanilate | 4.48 | 90 | 9 |

EXAMPLE 182

The primary use of acetanilideherbicides is for pre-emergent control of weeds by application of the herbicide to the soil before the plants emerge. This example illustrates the safening effect on alachlor herbicide when applied as a postemergent treatment on weeds in a crop of sorghum. Excellent weed control is shown with a substantial reduction in crop injury by the herbicide. The herbicide and antagonistic agent to be tested are applied in spray form to plants of a given age of several grasses and broadleaf species. In this test, one week after the plants are planted, each aluminum pan of plants is sprayed with a given volume of a solution of the desired percent concentration of the herbicide and antagonistic agent in sequence. The solution of safening agent is prepared by weighing the appropriate amount of agent in a suitable container, dissolving the safening agent in acetone and mixing the acetone solution with an approximately equal volume of water. The mixture of water and acetone solution is sprayed on the plants. The acetanilide herbicide along with a suitable emulsifying agent is dispersed in a suitable amount of water. The resulting water emulsion is then sprayed on the plants. The injuries to the plants are then observed approximately 21 days later and the results are recorded as percent inhibition of the plant. The results observed with respect to sorghum injury are presented in Table III.

EXAMPLE 183

The procedure of Example 182 is repeated except that the antagonistic agent is applied as a seed treatment rather than as a sequential spray before application of the herbicide. For seed treatment, the antagonistic agent is mixed with an inert carrier comprising a finely-divided clay and a high surface area calcium silicate in a range of weight percentages of active antagonistic agent to inert carrier. An excess of the antagonistic agent/inert carrier mixture is thoroughly mixed with the crop seed to be protected. With respect to sorghum seed, the following correlation of the composition of the mixture to the quantity of active ingredient per unit weight of sorghum seed is observed.

| Percent by weight of active antagonistic agent to inert carrier (% composition) | Percent by weight of active antagonistic agent to sorghum seed after treatment (% on seed) |
|---|---|
| 1.25 | 0.125 |
| 2.5 | 0.25 |
| 5 | 0.5 |
| 10 | 1.0 |

The results of applying antagonistic agents as a seed treatment of sorghum seed at various percentages and applying alachlor herbicide as a post-emergent herbicide at various application rates is shown in Table IV. Good control of weed species is observed.

TABLE III

| Amount of alachlor Herbicide (kg./ha.) | Antagonistic Agent | Amount (kg./ha.) | Percent Inhibition | Safening Effect (%) |
|---|---|---|---|---|
| 2.24 | Isopropyl-N-butylcarbanilate | 0.28 | 15 | 30 |
| 2.24 | Isopropyl-N-butylcarbanilate | 1.12 | 25 | 20 |
| 2.24 | Isopropyl-N-butylcarbanilate | 4.48 | 20 | 25 |
| 2.24 | Methyl-N-ethyl-dithiocarbanilate | 0.28 | 20 | 25 |

TABLE IV

| Amount of alachlor Herbicide (kg./ha.) | Antagonistic Agent | % On Seed Of Antagonistic Agent | Percent Inhibition | Safening Effect (%) |
|---|---|---|---|---|
| 1.12 | Isopropyl-N-butylcarbanilate | 0.25 | 28 | 45 |
| 2.24 | Isopropyl-N-butylcarbanilate | 0.25 | 43 | 37 |
| 4.48 | Isopropyl-N-butylcarbanilate | 0.25 | 50 | 20 |
| 1.12 | Isopropyl-N-butylcarbanilate | 1.00 | 58 | 15 |
| 2.24 | Isopropyl-N-butylcarbanilate | 1.00 | 58 | 22 |
| 4.48 | Isopropyl-N-butylcarbanilate | 1.00 | 60 | 10 |
| 1.12 | Methyl-N-ethyl-dithiocarbanilate | 0.125 | 33 | 40 |
| 2.24 | Methyl-N-ethyl-dithiocarbanilate | 0.125 | 75 | 5 |
| 1.12 | Methyl-N-ethyl-dithiocarbanilate | 0.50 | 53 | 20 |
| 2.24 | Methyl-N-ethyl-dithiocarbanilate | 0.50 | 58 | 22 |
| 0.56 | Allyl-N-methyl-dithiocarbanilate | 0.25 | 15 | 38 |
| 1.12 | Allyl-N-methyl-dithiocarbanilate | 0.25 | 35 | 50 |
| 2.24 | Allyl-N-methyl-dithiocarbanilate | 0.25 | 63 | 30 |
| 4.48 | Allyl-N-methyl-dithiocarbanilate | 0.25 | 85 | 10 |
| 0.56 | Allyl-N-methyl-dithiocarbanilate | 1.00 | 10 | 43 |
| 1.12 | Allyl-N-methyl-dithiocarbanilate | 1.00 | 20 | 65 |
| 2.24 | Allyl-N-methyl-dithiocarbanilate | 1.00 | 40 | 53 |
| 4.48 | Allyl-N-methyl-dithiocarbanilate | 1.00 | 78 | 17 |

EXAMPLES 184–202

These examples illustrate the application of the antagonistic agents of this invention as seed treatments to protect desired crops from herbicidal injury by acetanilide herbicides. In these examples the herbicide is applied to the soil as in Example 1–180. However, the antagonistic agent is applied to crop seed as in Example 183. The results are tabulated in Table V which show the safening effect of the antagonistic agents of this invention.

In order to counteract injury by the selective acetanilide herbicide, the crop seed need be treated with only a small amount of the antagonistic agent. For example, application rates of about 1100 g. to as low as about 1.5 g. of active agent per bushel of seed may be used. The presently preferred application rate is in the range of about 3 g. to 550 g. of agent per bushel. The seed is treated with an antagonistic agent by use of conventional seed treating apparatus well known to the art. The seed is thoroughly mixed with the antagonistic agent in the seed treating apparatus, thereby giving a seed which is coated with the agent.

Since only a very small amount of active antagonistic agent is required for the seed treatment, the compound preferably is formulated as a wettable powder or an emulsifiable concentrate which can be diluted with water by the seed treater for use in the seed treating apparatus. Of course, under certain conditions, it may be desirable to dissolve the antagonistic agent in an organic solvent for use as a seed treatment or the pure compound alone may be used under properly controlled conditions.

There are thus also provided by this invention novel seed treating compositions containing one or more of the described active antagonistic agents intimately dispersed in an inert carrier or diluent for the intended use. Such carriers may be either solids, such as talc, clay, diatomaceous earth, sawdust, calcium carbonate, and the like or liquids such as water, kerosene, acetone, benzene, toluene, xylene, and the like in which the active agent may be either dissolved or dispersed. Emulsifying agents are advisably used to achieve a suitable emulsion if two immiscible liquids are used as a carrier. Wetting agents may also be used to aid in dispersing the active antagonistic agent in liquids used as a carrier in which the agent is not completely soluble. Emulsifying agents and wetting agents, also known as "surface active agents," are sold under numerous tradenames and may be either pure compounds, mixtures of compounds of the same general groups, or they may be mixtures of compounds of different classes. Typical satisfactory surface active agents which may be used are alkali metal higher alkylarylsulfonates such as sodium dodecylbenzenesulfonate and the soldium salts of alkylnaphthalenesulfonic acids, fatty alcohol sulfates such as the sodium salts of monoesters of sulfuric acid with n-aliphatic alcohols containing 8–18 carbon atoms, long chain quaternary ammonium compounds, sodium salts of petroleum-derived alkylsulfonic acids, polyethylene sorbitan monooleate, alkylaryl polyether alcohols, water-soluble lignin sulfonate salts, alkali-casein compositions, long chain alcohols usually containing 10 to 18 carbon atoms, and condensation products of ethylene oxide with fatty acids, alkylphenols and mercaptans.

TABLE V

| Example Number | Amount of alachlor Herbicide (kg./ha.) | Antagonistic Agent | Weight % on Seed | Crop | Percent Inhibition | Safening Effect (%) |
|---|---|---|---|---|---|---|
| 184 | 0.28 | Isopropyl-N-butylcarbanilate | 0.25 | Sorghum | 0 | 78 |
|  | 0.28 | Isopropyl-N-butylcarbanilate | 0.50 | Sorghum | 0 | 78 |
|  | 0.28 | Isopropyl-N-butylcarbanilate | 1.00 | Sorghum | 5 | 73 |
|  | 0.56 | Isopropyl-N-butylcarbanilate | 0.25 | Sorghum | 0 | 75 |
|  | 0.56 | Isopropyl-N-butylcarbanilate | 0.50 | Sorghum | 5 | 70 |
|  | 0.56 | Isopropyl-N-butylcarbanilate | 1.00 | Sorghum | 10 | 65 |
|  | 1.12 | Isopropyl-N-butylcarbanilate | 0.25 | Sorghum | 0 | 93 |
|  | 1.12 | Isopropyl-N-butylcarbanilate | 0.50 | Sorghum | 0 | 93 |
|  | 1.12 | Isopropyl-N-butylcarbanilate | 1.00 | Sorghum | 10 | 83 |
|  | 2.24 | Isopropyl-N-butylcarbanilate | 0.25 | Sorghum | 25 | 75 |
|  | 2.24 | Isopropyl-N-butylcarbanilate | 0.50 | Sorghum | 0 | 100 |
|  | 2.24 | Isopropyl-N-butylcarbanilate | 1.00 | Sorghum | 0 | 100 |
| 185 | 0.28 | Methyldiethylthionocarbamate | 0.25 | Wheat | 0 | 13 |
|  | 0.28 | Methyldiethylthionocarbamate | 0.50 | Wheat | 0 | 13 |
|  | 0.28 | Methyldiethylthionocarbamate | 0.25 | Sorghum | 55 | 23 |
|  | 0.28 | Methyldiethylthionocarbamate | 0.50 | Sorghum | 65 | 13 |
| 186 | 0.28 | Methyl-N-ethyldithiocarbanilate | 0.25 | Wheat | 0 | 13 |
|  | 0.56 | Methyl-N-ethyldithiocarbanilate | 0.25 | Wheat | 5 | 10 |
|  | 1.12 | Methyl-N-ethyldithiocarbanilate | 0.25 | Wheat | 0 | 15 |
|  | 0.28 | Methyl-N-ethyldithiocarbanilate | 0.25 | Sorghum | 25 | 53 |
|  | 0.28 | Methyl-N-ethyldithiocarbanilate | 0.50 | Sorghum | 30 | 48 |
|  | 0.28 | Methyl-N-ethyldithiocarbanilate | 1.00 | Sorghum | 35 | 43 |
|  | 0.56 | Methyl-N-ethyldithiocarbanilate | 0.25 | Sorghum | 25 | 50 |
|  | 0.56 | Methyl-N- | 0.50 | Sorghum | 40 | 35 |

TABLE V-continued

| Example Number | Amount of alachlor Herbicide (kg./ha.) | Antagonistic Agent | Weight % on Seed | Crop | Percent Inhibition | Safening Effect (%) |
|---|---|---|---|---|---|---|
| | 0.56 | Methyl-N-ethyldithio-carbanilate | 1.00 | Sorghum | 40 | 35 |
| | 1.12 | Methyl-N-ethyldithio-carbanilate | 0.25 | Sorghum | 25 | 68 |
| | 1.12 | Methyl-N-ethyldithio-carbanilate | 0.50 | Sorghum | 25 | 68 |
| | 1.12 | Methyl-N-ethyldithio-carbanilate | 1.00 | Sorghum | 30 | 63 |
| | 2.24 | Methyl-N-ethyldithio-carbanilate | 0.25 | Sorghum | 40 | 60 |
| | 2.24 | Methyl-N-ethyldithio-carbanilate | 0.50 | Sorghum | 25 | 75 |
| | 2.24 | Methyl-N-ethyldithio-carbanilate | 1.00 | Sorghum | 50 | 50 |
| 187 | 0.28 | Isopropyl-N-butylcarbanilate | 0.016 | Sorghum | 45 | 30 |
| | 0.28 | Isopropyl-N-butylcarbanilate | 0.031 | Sorghum | 35 | 40 |
| | 0.28 | Isopropyl-N-butylcarbanilate | 0.063 | Sorghum | 35 | 40 |
| | 0.28 | Isopropyl-N-butylcarbanilate | 0.125 | Sorghum | 10 | 65 |
| | 0.28 | Isopropyl-N-butylcarbanilate | 0.25 | Sorghum | 15 | 60 |
| | 0.56 | Isopropyl-N-butylcarbanilate | 0.016 | Sorghum | 45 | 40 |
| | 0.56 | Isopropyl-N-butylcarbanilate | 0.031 | Sorghum | 50 | 35 |
| | 0.56 | Isopropyl-N-butylcarbanilate | 0.063 | Sorghum | 40 | 45 |
| | 0.56 | Isopropyl-N-butylcarbanilate | 0.125 | Sorghum | 15 | 70 |
| | 0.56 | Isopropyl-N-butylcarbanilate | 0.250 | Sorghum | 18 | 67 |
| | 1.12 | Isopropyl-N-butylcarbanilate | 0.016 | Sorghum | 65 | 27 |
| | 1.12 | Isopropyl-N-butylcarbanilate | 0.031 | Sorghum | 55 | 37 |
| | 1.12 | Isopropyl-N-butylcarbanilate | 0.063 | Sorghum | 50 | 42 |
| | 1.12 | Isopropyl-N-butylcarbanilate | 0.125 | Sorghum | 25 | 67 |
| | 1.12 | Isopropyl-N-butylcarbanilate | 0.250 | Sorghum | 40 | 52 |
| | 2.24 | Isopropyl-N-butylcarbanilate | 0.016 | Sorghum | 85 | 8 |
| | 2.24 | Isopropyl-N-butylcarbanilate | 0.031 | Sorghum | 85 | 8 |
| | 2.24 | Isopropyl-N-butylcarbanilate | 0.063 | Sorghum | 50 | 43 |
| | 2.24 | Isopropyl-N-butylcarbanilate | 0.125 | Sorghum | 40 | 53 |
| | 2.24 | Isopropyl-N-butylcarbanilate | 0.250 | Sorghum | 35 | 58 |
| 188 | 0.28 | Methyl-N-ethyldithiocarbanilate | 0.016 | Sorghum | 65 | 10 |
| | 0.28 | Methyl-N-ethyldithio-carbanilate | 0.031 | Sorghum | 50 | 25 |

TABLE V-continued

| Example Number | Amount of alachlor Herbicide (kg./ha.) | Antagonistic Agent | Weight % on Seed | Crop | Percent Inhibition | Safening Effect (%) |
|---|---|---|---|---|---|---|
| | 0.28 | Methyl-N-ethyldithio-carbanilate | 0.063 | Sorghum | 20 | 55 |
| | 0.28 | Methyl-N-ethyldithio-carbanilate | 0.125 | Sorghum | 15 | 60 |
| | 0.28 | Methyl-N-ethyldithio-carbanilate | 0.250 | Sorghum | 30 | 45 |
| | 0.56 | Methyl-N-ethyldithio-carbanilate | 0.016 | Sorghum | 65 | 20 |
| | 0.56 | Methyl-N-ethyldithio-carbanilate | 0.031 | Sorghum | 50 | 35 |
| | 0.56 | Methyl-N-ethyldithio-carbanilate | 0.063 | Sorghum | 25 | 60 |
| | 0.56 | Methyl-N-ethyldithio-carbanilate | 0.125 | Sorghum | 20 | 65 |
| | 0.56 | Methyl-N-ethyldithio-carbanilate | 0.250 | Sorghum | 35 | 50 |
| | 1.12 | Methyl-N-ethyldithio-carbanilate | 0.016 | Sorghum | 65 | 27 |
| | 1.12 | Methyl-N-ethyldithio-carbanilate | 0.031 | Sorghum | 70 | 22 |
| | 1.12 | Methyl-N-ethyldithio-carbanilate | 0.063 | Sorghum | 40 | 52 |
| | 1.12 | Methyl-N-ethyldithio-carbanilate | 0.125 | Sorghum | 35 | 57 |
| | 1.12 | Methyl-N-ethyldithio-carbanilate | 0.250 | Sorghum | 35 | 57 |
| | 2.24 | Methyl-N-ethyldithio-carbanilate | 0.016 | Sorghum | 80 | 13 |
| | 2.24 | Methyl-N-ethyldithio-carbanilate | 0.031 | Sorghum | 75 | 18 |
| | 2.24 | Methyl-N-ethyldithio-carbanilate | 0.063 | Sorghum | 60 | 33 |
| | 2.24 | Methyl-N-ethyldithio-carbanilate | 0.125 | Sorghum | 40 | 53 |
| | 2.24 | Methyl-N-ethyldithio-carbanilate | 0.250 | Sorghum | 35 | 58 |
| 189 | 0.14 | Allylthionocarbanilate | 0.016 | Sorghum | 70 | 15 |
| | 0.14 | Allylthionocarbanilate | 0.063 | Sorghum | 45 | 40 |
| | 0.28 | Allylthionocarbanilate | 0.063 | Sorghum | 65 | 34 |
| 190 | 0.14 | Allyl-N-methyldithio-carbanilate | 0.016 | Sorghum | 75 | 20 |
| | 0.14 | Allyl-N-methyldithio-carbanilate | 0.063 | Sorghum | 20 | 75 |
| | 0.14 | Allyl-N-methyldithio-carbanilate | 0.250 | Sorghum | 25 | 70 |
| | 0.14 | Allyl-N-methyldithio-carbanilate | 1.00 | Sorghum | 10 | 85 |
| | 0.28 | Allyl-N-methyldithio-carbanilate | 0.063 | Sorghum | 40 | 45 |
| | 0.28 | Allyl-N-methyldithio-carbanilate | 0.250 | Sorghum | 25 | 60 |
| | 0.28 | Allyl-N-methyldithio-carbanilate | 1.00 | Sorghum | 25 | 60 |
| | 0.56 | Allyl-N-methyldithio-carbanilate | 0.063 | Sorghum | 40 | 58 |

TABLE V-continued

| Example Number | Amount of alachlor Herbicide (kg./ha.) | Antagonistic Agent | Weight % on Seed | Crop | Percent Inhibition | Safening Effect (%) |
|---|---|---|---|---|---|---|
| | 0.56 | Allyl-N-methyldithio-carbanilate | 0.250 | Sorghum | 25 | 73 |
| | 0.56 | Allyl-N-methyldithio-carbanilate | 1.00 | Sorghum | 20 | 78 |
| | 1.12 | Allyl-N-methyldithio-carbanilate | 0.063 | Sorghum | 50 | 50 |
| | 1.12 | Allyl-N-methyldithio-carbanilate | 0.250 | Sorghum | 45 | 55 |
| | 1.12 | Allyl-N-methyldithio-carbanilate | 1.00 | Sorghum | 45 | 55 |
| | 2.24 | Allyl-N-methyldithio-carbanilate | 0.063 | Sorghum | 65 | 35 |
| | 2.24 | Allyl-N-methyldithio-carbanilate | 0.250 | Sorghum | 60 | 40 |
| | 2.24 | Allyl-N-methyldithio-carbanilate | 1.00 | Sorghum | 55 | 45 |
| 191 | 0.28 | Allyl-thiono-carbanilate | 0.25 | Wheat | 30 | 13 |
| | 0.56 | Allyl-thiono-carbanilate | 0.25 | Wheat | 15 | 48 |
| | 1.12 | Allyl-thiono-carbanilate | 0.25 | Wheat | 40 | 33 |
| | 2.24 | Allyl-thiono-carbanilate | 0.25 | Wheat | 55 | 25 |
| | 4.48 | Allyl-thiono-carbanilate | 0.25 | Wheat | 60 | 33 |
| 192 | 0.28 | Allyl-N-methyldithio-carbanilate | 1.00 | Wheat | 20 | 23 |
| | 0.56 | Allyl-N-methyldithio-carbanilate | 1.00 | Wheat | 25 | 38 |
| | 1.12 | Allyl-N-methyldithio-carbanilate | 1.00 | Wheat | 55 | 28 |
| | 2.24 | Allyl-N-methyldithio-carbanilate | 1.00 | Wheat | 65 | 15 |
| | 4.48 | Allyl-N-methyldithio-carbanilate | 1.00 | Wheat | 65 | 28 |
| 193 | 0.28 | 2-Chloroallyl-o-chloro-N-(2-chloroallyl)di-thiocarbanilate | 1.00 | Wheat | 10 | 33 |
| | 0.56 | 2-Chloroallyl-o-chloro-N-(2-chloroallyl)di-thiocarbanilate | 1.00 | Wheat | 15 | 48 |
| | 1.12 | 2-Chloroallyl-o-chloro-N-(2-chloroallyl)di-thiocarbanilate | 1.00 | Wheat | 25 | 48 |
| | 2.24 | 2-Chloroallyl-o-chloro-N-(2-chloroallyl)di-thiocarbanilate | 1.00 | Wheat | 45 | 35 |
| | 4.48 | 2-Chloroallyl-o-chloro-N-(2-chloroallyl)di-thiocarbanilate | 1.00 | Wheat | 60 | 33 |
| 194 | 0.28 | Allyl-N-methyldithio-carbanilate | 0.063 | Wheat | 15 | 35 |
| | 0.28 | Allyl-N-methyldithio-carbanilate | 0.25 | Wheat | 30 | 20 |
| | 0.56 | Allyl-N-methyldithio-carbanilate | 0.25 | Wheat | 60 | 10 |
| | 1.12 | Allyl-N-methyldithio-carbanilate | 0.25 | Wheat | 60 | 15 |
| | 0.28 | Allyl-N-methyldithio- | 1.00 | Wheat | 30 | 20 |

TABLE V-continued

| Example Number | Amount of alachlor Herbicide (kg./ha.) | Antagonistic Agent | Weight % on Seed | Crop | Percent Inhibition | Safening Effect (%) |
|---|---|---|---|---|---|---|
| | 0.56 | Allyl-N-methyldithiocarbanilate | 1.00 | Wheat | 40 | 30 |
| | 1.12 | Allyl-N-methyldithiocarbanilate | 1.00 | Wheat | 60 | 15 |
| 195 | 0.14 | 2-chloroallyl-o-chloro-N-(2-chloroallyl)dithiocarbanilate | 0.016 | Wheat | 0 | 25 |
| | 0.56 | 2-chloroallyl-o-chloro-N-(2-chloroallyl)dithiocarbanilate | 0.016 | Wheat | 40 | 20 |
| | 0.14 | 2-chloroallyl-o-chloro-N-(2-chloroallyl)dithiocarbanilate | 0.063 | Wheat | 0 | 25 |
| | 0.14 | 2-chloroallyl-o-chloro-N-(2-chloroallyl)dithiocarbanilate | 0.25 | Wheat | 0 | 25 |
| | 0.28 | 2-chloroallyl-o-chloro-N-(2-chloroallyl)dithiocarbanilate | 0.25 | Wheat | 20 | 30 |
| | 1.12 | 2-chloroallyl-o-chloro-N-(2-chloroallyl)dithiocarbanilate | 0.25 | Wheat | 60 | 15 |
| 196 | 0.07 | Allyl-N-methyldithiocarbanilate | 1.0 | Sorghum | 5 | 75 |
| | 0.14 | Allyl-N-methyldithiocarbanilate | 1.0 | Sorghum | 0 | 90 |
| | 0.28 | Allyl-N-methyldithiocarbanilate | 1.0 | Sorghum | 10 | 85 |
| | 0.56 | Allyl-N-methyldithiocarbanilate | 1.0 | Sorghum | 15 | 85 |
| | 1.12 | Allyl-N-methyldithiocarbanilate | 1.0 | Sorghum | 25 | 75 |
| | 2.24 | Allyl-N-methyldithiocarbanilate | 1.0 | Sorghum | 40 | 60 |
| | 0.07 | Allyl-N-methyldithiocarbanilate | 2.0 | Sorghum | 0 | 80 |
| | 0.14 | Allyl-N-methyldithiocarbanilate | 2.0 | Sorghum | 0 | 90 |
| | 0.28 | Allyl-N-methyldithiocarbanilate | 2.0 | Sorghum | 10 | 85 |
| | 0.56 | Allyl-N-methyldithiocarbanilate | 2.0 | Sorghum | 15 | 85 |
| | 1.12 | Allyl-N-methyldithiocarbanilate | 2.0 | Sorghum | 15 | 85 |
| | 2.24 | Allyl-N-methyldithiocarbanilate | 2.0 | Sorghum | 40 | 60 |
| | 0.07 | Allyl-N-methyldithiocarbanilate | 4.0 | Sorghum | 5 | 75 |
| | 0.14 | Allyl-N-methyldithiocarbanilate | 4.0 | Sorghum | 0 | 90 |
| | 0.28 | Allyl-N-methyldithiocarbanilate | 4.0 | Sorghum | 10 | 85 |
| | 0.56 | Allyl-N-methyldithiocarbanilate | 4.0 | Sorghum | 20 | 80 |
| | 1.12 | Allyl-N-methyldithiocarbanilate | 4.0 | Sorghum | 20 | 80 |
| | 2.24 | Allyl-N-methyldithiocarbanilate | 4.0 | Sorghum | 40 | 60 |
| 197 | 0.28 | 2-Cyclohexen-1-yldiisopropylthiolcar- | 0.25 | Wheat | 40 | 20 |

TABLE V-continued

| Example Number | Amount of alachlor Herbicide (kg./ha.) | Antagonistic Agent | Weight % on Seed | Crop | Percent Inhibition | Safening Effect (%) |
|---|---|---|---|---|---|---|
| 198 | 0.14 | Isopropylhex-ahydroazocine-1(2H)-carbothionate | 0.063 | Wheat | 15 | 15 |
| | 0.28 | Isopropylhex-ahydroazocine-1(2H)-carbothionate | 0.063 | Wheat | 20 | 30 |
| | 0.56 | Isopropylhex-ahydroazocine-1(2H)-carbothionate | 0.063 | Wheat | 30 | 50 |
| | 1.12 | Isopropylhex-ahydroazocine-1(2H)-carbothionate | 0.063 | Wheat | 35 | 40 |
| | 2.24 | Isopropylhex-ahydroazocine-1(2H)-carbothionate | 0.063 | Wheat | 65 | 20 |
| | 0.14 | Isopropylhex-ahydroazocine-1(2H)-carbothionate | 0.25 | Wheat | 15 | 15 |
| | 0.28 | Isopropylhex-ahydroazocine-1(2H)-carbothionate | 0.25 | Wheat | 20 | 30 |
| | 0.56 | Isopropylhex-ahydroazocine-1(2H)-carbothionate | 0.25 | Wheat | 20 | 60 |
| | 1.12 | Isopropylhex-ahydroazocine-1(2H)-carbothionate | 0.25 | Wheat | 30 | 45 |
| | 2.24 | Isopropylhex-ahydroazocine-1(2H)-carbothionate | 0.25 | Wheat | 40 | 45 |
| 199 | 0.14 | Ethyloctahydro-(1H)azoninecarbothionate | 0.063 | Wheat | 0 | 15 |
| | 0.28 | Ethyloctahydro-(1H)azoninecarbothionate | 0.063 | Wheat | 5 | 60 |
| | 0.56 | Ethylocta-hydro(1H)azoninecarbothionate | 0.063 | Wheat | 20 | 45 |
| | 1.12 | Ethylocta-hydro(1H)azoninecarbothionate | 0.063 | Wheat | 15 | 55 |
| | 2.24 | Ethylocta-hydro(1H)azoninecarbothionate | 0.063 | Wheat | 60 | 20 |
| | 0.14 | Ethylocta-hydro(1H)azoninecarbothionate | 0.25 | Wheat | 0 | 15 |
| | 0.28 | Ethylocta-hydro(1H)azoninecarbothionate | 0.25 | Wheat | 25 | 40 |
| | 0.56 | Ethylocta-hydro(1H)azoninecarbothionate | 0.25 | Wheat | 20 | 45 |
| | 1.12 | Ethylocta-hydro(1H)azoninecarbothionate | 0.25 | Wheat | 25 | 45 |
| | 2.24 | Ethylocta-hydro(1H)azoninecarbothionate | 0.25 | Wheat | 35 | 45 |
| 200 | 0.14 | Benzyliso-butyldithio-carbamate | 0.063 | Wheat | 10 | 15 |
| | 0.28 | Benzyliso-butyldithio-carbamate | 0.063 | Wheat | 20 | 45 |
| | 0.56 | Benzyliso-butyldithio-carbamate | 0.063 | Wheat | 30 | 45 |
| | 0.28 | Benzyliso-butyldithio-carbamate | 0.25 | Wheat | 15 | 50 |
| | 0.56 | Benzyliso-butyldithio-carbamate | 0.25 | Wheat | 15 | 60 |
| | 1.12 | Benzyliso-butyldithio-carbamate | 0.25 | Wheat | 30 | 40 |
| | 2.24 | Benzyliso-butyldithio-carbamate | 0.25 | Wheat | 50 | 30 |
| 201 | 0.14 | Methyl-N-methyldithio-carbanilate | 0.063 | Wheat | 0 | 10 |
| | 0.28 | Methyl-N-methyldithio-carbanilate | 0.063 | Wheat | 0 | 55 |

TABLE V-continued

| Example Number | Amount of alachlor Herbicide (kg./ha.) | Antagonistic Agent | Weight % on Seed | Crop | Percent Inhibition | Safening Effect (%) |
|---|---|---|---|---|---|---|
| | 0.56 | Methyl-N-methyldithio-carbanilate | 0.063 | Wheat | 45 | 20 |
| | 1.12 | Methyl-N-methyldithio-carbanilate | 0.063 | Wheat | 55 | 35 |
| | 2.24 | Methyl-N-methyldithio-carbanilate | 0.063 | Wheat | 60 | 30 |
| | 0.14 | Methyl-N-methyldithio-carbanilate | 0.25 | Wheat | 0 | 10 |
| | 0.28 | Methyl-N-methyldithio-carbanilate | 0.25 | Wheat | 0 | 55 |
| | 0.56 | Methyl-N-methyldithio-carbanilate | 0.25 | Wheat | 0 | 65 |
| | 1.12 | Methyl-N-methyldithio-carbanilate | 0.25 | Wheat | 15 | 75 |
| | 2.24 | Methyl-N-methyldithio-carbanilate | 0.25 | Wheat | 25 | 65 |
| | 0.28 | Methyl-N-methyldithio-carbanilate | 1.0 | Wheat | 20 | 35 |
| | 0.56 | Methyl-N-methyldithio-carbanilate | 1.0 | Wheat | 15 | 50 |
| | 1.12 | Methyl-N-methyldithio-carbanilate | 1.0 | Wheat | 25 | 65 |
| | 2.24 | Methyl-N-methyldithio-carbanilate | 1.0 | Wheat | 25 | 65 |
| 202 | 0.14 | Phenyldiethyldithio-carbanilate | 0.25 | Sorghum | 0 | 15 |
| | 0.28 | Phenyldiethyldithio-carbanilate | 0.25 | Sorghum | 0 | 35 |
| | 0.56 | Phenyldiethyldithio-carbanilate | 0.25 | Sorghum | 10 | 55 |
| | 1.12 | Phenyldiethyldithio-carbanilate | 0.25 | Sorghum | 15 | 75 |
| | 0.56 | Phenyldiethyldithio-carbanilate | 1.0 | Sorghum | 40 | 25 |
| | 1.12 | Phenyldiethyldithio-carbanilate | 1.0 | Sorghum | 50 | 40 |

The safening results found in greenhouse tests are substantiated by field tests of a representative antagonistic agent, allyl-N-methyldithiocarbanilate. Good results are obtained when sorghum and wheat seed is treated with this antagonistic agent formulated with a variety of liquid carriers such as ketone solvents, for example acetone, chlorinated hydrocarbon solvents, for example dichloromethane, aromatic solvents, for example toluene and ester solvents, for example ethyl acetate, as well as a variety of solid diluents such as clays, silicates and combinations of clays and silicates. The preferred concentrations of solid formulations range from about 10 percent to about 50 percent by weight of active antagonistic agent to total formulation weight.

While this invention has been described with respect to certain embodiments, it is to be understood that it is not so limited and that variations and modifications thereof obvious to those skilled in the art to which this invention appertains can be made without departing from the spirit or scope thereof.

What is claimed is:

1. A method for reducing injury to crops by α-haloacetanilide herbicides which comprises applying to the soil, crop, or crop seed an effective safening amount of a compound of the formula

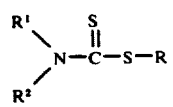

wherein R is $C_{1-8}$ alkyl, $C_{2-8}$ alkenyl or haloalkenyl, phenyl, cyanomethyl, cyclohexyl, cyclohexenyl, benzyl or benzyl substituted with halo, nitro or trifluoromethyl groups; $R^1$ is $C_{1-8}$ alkyl, $C_{2-8}$ alkenyl, phenyl or phenyl substituted with halo, nitro or lower alkyl groups and $R^2$ is hydrogen, $C_{1-8}$ alkyl or $C_{2-8}$ alkenyl or haloalkenyl.

2. A method of claim 1 wherein the crops are wheat and sorghum.

3. A method of claim 1 wherein the acetanilide is α-chloroacetanilide.

4. A method of claim 1 wherein the compound is applied to the soil.

5. A method of claim 4 wherein the compound is applied to the soil and incorporated into the soil.

6. A method of claim 4 wherein the compound is applied to the soil dispersed in a liquid carrier.

7. A method of claim 4 wherein the compound is applied to the soil dispersed on a particulate solid carrier.

8. A method of claim 1 wherein the compound is applied to the seed.

9. A method of claim 8 wherein the compound is applied to the seed dispersed in a liquid carrier.

10. A method of claim 8 wherein the compound is applied to the seed dispersed on a particulate solid carrier.

11. A method of claim 1 wherein $R^1$ is phenyl or phenyl substituted with halo, nitro or lower alkyl groups.

12. A method of claim 11 wherein R is $C_{1-6}$ alkyl.

13. A method of claim 12 wherein $R^2$ is hydrogen.

14. A method of claim 12 wherein $R^2$ is $C_{1-6}$ alkyl.

15. A method of claim 12 wherein $R^2$ is $C_{2-8}$ alkenyl.

16. A method of claim 12 wherein $R^2$ is $C_{2-8}$ haloalkenyl.

17. A method of claim 11 wherein R is $C_{2-8}$ alkenyl.

18. A method of claim 17 wherein $R^2$ is hydrogen.

19. A method of claim 17 wherein $R^2$ is $C_{1-6}$ alkyl.

20. A method of claim 17 wherein $R^2$ is $C_{2-8}$ alkenyl.

21. A method of claim 17 wherein $R^2$ is $C_{2-8}$ haloalkenyl.

22. A method of claim 11 wherein R is phenyl.

23. A method of claim 1 wherein R is cyclohexyl or cyclohexenyl.

24. A method of claim 11 wherein R is $C_{2-8}$ haloalkenyl.

25. A method of claim 1 wherein $R^1$ is $C_{1-6}$ alkyl.

26. A method of claim 25 wherein R is $C_{1-6}$ alkyl.

27. A method of claim 26 wherein $R^2$ is $C_{1-6}$ alklyl.

28. Method of claim 3 wherein said $\alpha$-chloroacetanilide is alachlor.

29. Method of claim 19 wherein said compound is allyl N-methyldithiocarbanilate.

30. A method of claim 1 wherein R is benzyl or benzyl substituted with halogen or trifluoromethyl.

* * * * *